(12) United States Patent
Brown

(10) Patent No.: US 10,603,453 B2
(45) Date of Patent: Mar. 31, 2020

(54) HALOCARBON RECYCLING METHODS AND SYSTEMS

(71) Applicant: SAGETECH MEDICAL EQUIPMENT LIMITED, Surrey (GB)

(72) Inventor: Sebastian Matthew Brown, Totnes (GB)

(73) Assignee: SAGETECH MEDICAL EQUIPMENT LIMITED, Surrey (GB)

(*) Notice: Subject to any disclaimer, the term of this patent is extended or adjusted under 35 U.S.C. 154(b) by 316 days.

(21) Appl. No.: 15/505,009

(22) PCT Filed: Aug. 20, 2015

(86) PCT No.: PCT/GB2015/052426
§ 371 (c)(1),
(2) Date: Feb. 17, 2017

(87) PCT Pub. No.: WO2016/027097
PCT Pub. Date: Feb. 25, 2016

(65) Prior Publication Data
US 2018/0110947 A1    Apr. 26, 2018

(30) Foreign Application Priority Data
Aug. 20, 2014  (GB) .................................. 1414820.9

(51) Int. Cl.
*A61M 16/00* (2006.01)
*B01J 20/20* (2006.01)
(Continued)

(52) U.S. Cl.
CPC ...... *A61M 16/0093* (2014.02); *A61M 16/104* (2013.01); *A61M 16/105* (2013.01);
(Continued)

(58) Field of Classification Search
CPC .... A61M 16/18; A61M 16/009; A61M 16/12; A61M 16/0093; A61M 16/104;
(Continued)

(56) References Cited

U.S. PATENT DOCUMENTS 4,308,038 A * 12/1981 Michel ...................... B03C 3/15
                                                    261/112.1
4,905,685 A *  3/1990 Olsson ................ A61M 16/009
                                                    128/203.12
(Continued)

FOREIGN PATENT DOCUMENTS

CA          1339833      3/1988
CN        102574098      7/2012
(Continued)

OTHER PUBLICATIONS

Chinese patent application No. 201580044784.0—Second Office Action dated Mar. 20, 2019 by the State Intellectual Property Office of the People's Republic of China; pp. 1-4.
(Continued)

*Primary Examiner* — Manuel A Mendez
(74) *Attorney, Agent, or Firm* — Nicholas J. Landau; Jessica Zurlo; Bradley Arant Boult Cummings LLP

(57) ABSTRACT

A method for capturing halocarbon from a gas, the method comprising processing gas containing halocarbon with material which is undamaged by exposure to supercritical fluid. A method for reclaiming halocarbon from a material, the method comprising exposing the material to a supercritical fluid. A module for processing a gas containing halocarbon, the module comprising material for capturing halocarbon from a gas, wherein the module is arranged to withstand supercritical fluid.

28 Claims, 12 Drawing Sheets

(51) Int. Cl.
| | |
|---|---|
| *B01J 20/10* | (2006.01) |
| *B01J 20/28* | (2006.01) |
| *B01D 53/04* | (2006.01) |
| *A61M 16/10* | (2006.01) |
| *A61M 16/12* | (2006.01) |
| *B01J 20/06* | (2006.01) |
| *B01J 20/16* | (2006.01) |
| *B01J 20/24* | (2006.01) |
| *B01D 3/14* | (2006.01) |
| *A61M 16/08* | (2006.01) |
| *A61M 16/01* | (2006.01) |
| *A61M 16/18* | (2006.01) |
| *A61M 16/22* | (2006.01) |
| *A61M 16/20* | (2006.01) |

(52) U.S. Cl.
CPC .............. *A61M 16/12* (2013.01); *B01D 3/14* (2013.01); *B01D 53/0423* (2013.01); *B01J 20/06* (2013.01); *B01J 20/103* (2013.01); *B01J 20/16* (2013.01); *B01J 20/165* (2013.01); *B01J 20/20* (2013.01); *B01J 20/205* (2013.01); *B01J 20/24* (2013.01); *B01J 20/28047* (2013.01); *A61M 16/0078* (2013.01); *A61M 16/01* (2013.01); *A61M 16/0891* (2014.02); *A61M 16/18* (2013.01); *A61M 16/208* (2013.01); *A61M 16/209* (2014.02); *A61M 16/22* (2013.01); *A61M 2202/0208* (2013.01); *A61M 2202/0225* (2013.01); *A61M 2202/0241* (2013.01); *A61M 2202/0283* (2013.01); *A61M 2205/7581* (2013.01); *B01D 2253/25* (2013.01); *B01D 2256/26* (2013.01); *B01D 2257/206* (2013.01); *B01D 2259/124* (2013.01); *B01D 2259/40001* (2013.01); *B01D 2259/4533* (2013.01)

(58) Field of Classification Search
CPC . A61M 16/01; F25J 3/08; B01J 20/20; G01N 33/1846; G01N 1/2202; Y02P 20/544; C10J 3/84; Y02A 50/235; Y02A 50/2342; B01D 53/04; B01D 53/1475; B01D 53/02; B01D 53/62; B01D 53/0454; B01D 53/0462; B01D 53/047; B01D 53/1425; A61K 31/05
See application file for complete search history.

(56) References Cited

U.S. PATENT DOCUMENTS

| | | | |
|---|---|---|---|
| 5,205,154 A | | 4/1993 | Lee et al. |
| 2002/0020462 A1 | | 2/2002 | Wagenheim |
| 2003/0044514 A1 | | 3/2003 | Richard |
| 2003/0139681 A1* | | 7/2003 | Melker ................ A61B 5/0836 600/532 |
| 2006/0008506 A1* | | 1/2006 | Cipriano De Sousa ..................... A61K 9/0051 424/427 |
| 2006/0107831 A1* | | 5/2006 | Karwacki, Jr. ......... B01D 53/04 95/116 |
| 2012/0222556 A1* | | 9/2012 | Filipovic ............. A61M 16/009 95/142 |

FOREIGN PATENT DOCUMENTS

| | | |
|---|---|---|
| EP | 0682980 | 5/1995 |
| EP | 0677332 | 10/1995 |
| EP | 1911481 | 4/2008 |
| JP | 2-277505 | 11/1990 |
| JP | 4-256401 | 9/1992 |
| JP | 06-170111 | 6/1994 |
| JP | 9-206044 | 8/1997 |
| JP | 2004-174387 | 11/2002 |
| JP | 2004-174387 | 6/2004 |
| JP | 2005-195398 | 7/2005 |
| JP | 2005-279473 | 10/2005 |
| JP | 2010-243258 | 10/2010 |
| JP | 2013-503039 | 1/2013 |
| SE | 1130026 | 11/2012 |
| WO | 00/72861 | 12/2000 |
| WO | 2011/026230 | 3/2011 |
| WO | 2011026230 | 3/2011 |
| WO | 2012064245 | 5/2012 |

OTHER PUBLICATIONS

Cowell, Gabrielle "Great Britain Search Report—Application No. GB1414820.9" United Kingdom Intellectual Property Office; dated Feb. 25, 2015, pp. 1-4.

Phlmann, Robert "International Search Report and Written Opinion—PCT/GB2015/052426" European Patent Office as International Searching Authority; dated Apr. 14, 2016, pp. 1-26.

Sugisaki, Satoru "Office Action issued in Japanese co-pending application No. 2017-529160" dated Feb. 28, 2018; Japanese Patent Office; pp. 1-6.

"Office Action issued in co-pending Chinese Application No. 201580044784.0" The State Intellectual Property Office of People's Republic of China; dated Dec. 2, 2019.

Jihong Zhang "Green Chemistry" Anhui Normal University Press; Aug. 30, 2012.

Shinya Mashiyma "Notification of Reasons for Refusal—Japanese patent application No. 2019-016655" Japanese Patent Office; dated Nov. 27, 2019; pp. 1-11.

* cited by examiner

HALOCARBON RECYCLING METHODS AND SYSTEMS

CROSS-REFERENCE TO RELATED APPLICATIONS

This application is a national stage under 35 U.S.C. 371 of International Application PCT/GB2015/052426, filed on Aug. 20, 2015 (currently published). International Application PCT/GB2015/052426 cites the priority of Great Britain Patent Application No. 1414820.9, filed Aug. 20, 2014 (expired).

TECHNICAL FIELD

The present invention relates to methods and systems for capturing and recycling halocarbons. In particular, the present invention relates to methods and systems for capturing and recycling halocarbons when used as volatile anaesthetic agents in medical environments.

BACKGROUND

A halocarbon is an organic chemical molecule composed of at least one carbon atom bound covalently with one or more halocarbon atoms. Halocarbons have many uses and are used in several industries as solvents, pesticides, refrigerants, fire-resistant oils, ingredients of elastomers, adhesives and sealants, electrically insulating coatings, plastics and anaesthetics. An alternative term for halocarbons is "halocarbonated fluorocarbons".

Examples of halocarbons which are used as anaesthetic agents typically include desflurane, isoflurane, sevoflurane, halothane and enflurane. These anaesthetics may be referred to as volatile anaesthetic agents because they are liquid at room temperature but evaporate easily to produce a vapour for inhalation by a patient to induce anaesthesia. These agents are administered to patients using the breathing circuit of an anaesthetic machine, also known as a Boyle's machine. A schematic diagram of part of an anaesthetic machine including its breathing circuit 2 is described below with reference to FIG. 1. The primary function of the anaesthetic machine is to mix oxygen with volatile anaesthetic agent, at a clinician-specified concentration, for delivery to the patient via the breathing circuit 2.

The anaesthetic machine and breathing circuit 2 comprises a network of piped gas for inhalation by a patient (not shown). Air, oxygen ($O_2$) and nitrous oxide ($N_2O$) are supplied respectively to the back bar 15 from an air pipe 3 or an air cylinder pipe 5, an oxygen pipe 7 or an oxygen cylinder pipe 9 and a nitrous oxide pipe 11 or a nitrous oxide cylinder pipe 13. Each gas pipe 3, 7, 11 supplies gas at 4 bar. Air and oxygen are supplied by cylinder pipes 5, 9, at 137 bar. Nitrous oxide is supplied by cylinder pipe 13 at 44 bar. To reduce the pressure of the gases supplied by the cylinder pipes 5, 9, 13 to match the pressure of the gases supplied by the gas pipe 3, 7, 11 each cylinder pipe 5, 9, 13 comprises a pressure reducing valve (PRV) 17 which reduces the pressure of gases supplied by the cylinder pipes 5, 9, 13 to 4 bar.

Each of the air, oxygen and nitrous oxide is delivered separately to a respective variable flow valve 19, which allows an anaesthetist to mix the air, oxygen and nitrous oxide as required. Each variable flow valve 19 further reduces the pressure of the gases to just over 1 bar. FIG. 1 shows the gases are delivered to the back bar 15, from left to right, via an air back bar pipe 18, an oxygen back bar pipe 20 and a nitrous oxide back bar pipe 22. It will be immediately apparent to the skilled person that the back bar pipes 18, 20, 22 may be arranged differently. For example, the back bar pipes 18, 20, 22 may be arranged from left to right in FIG. 1 in the following order: the nitrous oxide back bar pipe 22; the oxygen back bar pipe 20; and the air back bar pipe 18.

The back bar 15 comprises a vaporiser 10 and a pressure relief valve 16. The vaporiser 10 contains a vaporisation chamber 21 in which the agent 12 is housed. The vaporisation chamber 21 is arranged so that the agent 12 evaporates to form vapour 14 at the saturated vapour pressure of the agent 12. For example, if the saturated vapour pressure is at too high a concentration to deliver agent 12 to the patient, a variable bypass valve 23 allows the anaesthetist to control the fraction of gases supplied from the back bar 15 that pass through the vaporiser 10. Accordingly, the output concentration of volatile agent 12 within the gas flow leaving the back bar 15 is controlled.

The patient inhales gases via a face mask 4 which fits over and forms a seal around the patient's nose and mouth. The face mask 4 is connected to an inspiratory tube 6 which supplies gases containing an anaesthetic agent 12, and an expiratory tube 8 through which exhaled and unused gases and agent 12 are transported away from the patient. The inspiratory tube 6 and expiratory tube 8 are typically corrugated hoses.

The inspiratory tube 6 comprises a unidirectional inspiratory valve 25 which opens upon inhalation by the patient. When the unidirectional inspiratory valve 25 is in an open state, gas flows through the back bar 15, through the vaporisation chamber 10 where it mixes with vapour 14 from the agent 12. The gas mixed with agent vapour 14 is inhaled by the patient. In use, the breathing circuit 2 dispenses an accurate and continuous supply of anaesthetic agent mixed with oxygen/air/nitrous oxide ($N_2O$) at a specific concentration to the patient at a safe pressure and flow rate.

The expiratory tube 8 is connected to an expiratory pipe 24 to which is connected a unidirectional expiratory valve 26 through which exhaled and unused gases pass when the unidirectional expiratory valve 26 is open. Gas that passes through the unidirectional expiratory valve 26 flows into a breathing bag 28. An exhaust pipe 30 leads from the breathing bag 28 to a variable pressure-relief valve 32.

A carbon dioxide ($CO_2$) absorber canister 34 is connected to the expiratory pipe 24 and the inspiratory pipe 15 and arranged to allow gases to flow through the absorber canister 34 from the expiratory pipe 24 to the inspiratory pipe 6. The absorber canister 34 contains soda lime 36 which absorbs carbon dioxide from the gas that flows through the canister 34.

The configuration of the breathing circuit 2 illustrated in FIG. 1 is shown during inhalation of the gas/agent mixture by the patient. The movement of inhaled gases is shown by the solid arrows and the movement of exhaled gases is shown using dashed arrows.

Inhalation by the patient causes the expiratory valve 26 to close and the inspiratory valve 25 to open. This allows recirculated gas to flow from the breathing bag 28, through the absorption canister 34 which absorbs $CO_2$ in the gas, and into the inspiratory pipe 6. The gas passes through the vaporisation chamber 10 where it mixes with the agent vapour 14. The resultant gas/agent mixture is administered to the patient via the unidirectional inspiratory valve 25 and inspiratory limb 6 of the breathing circuit 2 and the breathing mask 4. The patient breathes the gas/agent mixture into their lungs which dissolve some of the agent vapour 14 into the patient's blood. This leads to a reversible state of anaesthesia.

Upon exhalation by the patient, the expiratory valve 26 opens and the inspiratory valve 25 closes. The gases exhaled by the patient, including the portion of the agent vapour 14 that is not absorbed by the patient, flow back into the breathing circuit 2 via the expiratory tube 8. The exhaled gases flow into the breathing bag 28 and excess waste gas 38 is vented via the pressure-relief valve 32. A waste pipe 40 guides the vented waste gas 38 from the breathing circuit 2.

The vented waste gas 38 will contain at least trace amounts of unused anaesthetic agent vapour 14. Even trace amounts of anaesthetic in the air in a medical environment will have an effect on medical staff, continued exposure to which will cause adverse health conditions, such as headache, increased incidence of spontaneous abortion, congenital anomalies in babies and haematological malignancy. Accordingly, governmental agencies have set limits on the level of volatile anaesthetic agent that hospital staff may be exposed to. In the USA the level of volatile anaesthetic agent in the air of an operating theatre should not exceed 2 parts per million (ppm), and the level of $N_2O$ should not exceed 25 ppm. The limit set for volatile agent in the UK is 50 ppm, and for $N_2O$ the limit is set at 100 ppm.

In order to ensure that the environment within operating theatres and other medical environments stay within the above limits, the waste gas 38 which contains volatile anaesthetic agent vapour 14 is prevented from entering the atmosphere of medical environments.

To prevent the release of anaesthetic gases into the atmosphere of an operating theatre, in most developed countries, the waste gas 38 is "scavenged". In hospitals and large veterinary practices, operating theatre suites are provided with a negative pressure circuit. The negative pressure circuit is connected to the exhaust pipe 40 of the anaesthetic machine. The negative pressure circuit extracts the waste gas 38 to the atmosphere via an output pipe at the top of the building. Anaesthetic users of smaller practices extract waste gas 38 from the exhaust pipe 40 using the circuit pressure following the variable pressure release valve 32, which is at a pressure lower than the breathing circuit, to pass waste gases 38 from the exhaust pipe 40 through activated charcoal canisters. Such charcoal canisters are typically able to absorb twelve hours of waste gas 38. However, a problem with charcoal canisters is that once they have been used they cannot be recycled and must be disposed of, which is costly. Furthermore, unused volatile agent captured by the activated charcoal canisters may be slowly released after disposal.

Volatile anaesthetic agents are halogenated fluorocarbons, and therefore their release directly into the atmosphere is particularly undesirable. Halocarbons containing bromine and chlorine groups, collectively referred to as chloroflouorocarbons (CFCs), exert a damaging effect on the ozone layer. Indeed, the release of CFCs from any industry is damaging to the ozone layer. In the stratosphere, light at higher wavelength breaks down the C—Cl/Br bond of CFCs which releases highly reactive free radical groups that break down ozone ($O_3$), depleting the earth's UV protective barrier. Isoflurane and halothane are both CFCs. Each agent has a different reactivity due to the amount of free radical each agent releases, and the ease with which the carbon-halide group is broken. Halothane is the most reactive, due to the relative ease with which the Br group may be removed from the molecule, followed by isoflurane. Nitrous oxide ($N_2O$) also has some ozone depleting potential.

In addition, $N_2O$ and all agents, including sevoflurane and desflurane, are potent greenhouse gases due to their ability to absorb infrared light. Desflurane is the most potent due to its long atmospheric half-life. One kilo of Desflurane is equivalent to approximately 2000-3500 kg of $CO_2$.

The use of CFCs was curbed by the Montreal agreement in 1987 (and subsequent amendments). As a result, the use of CFCs in refrigeration and aerosols was banned and all CFC use not deemed 'essential' was monitored. Medical uses of CFCs are deemed 'essential' and are therefore unmonitored. With the banning of the use of CFCs in refrigeration and aerosols, the proportion of halocarbons released into the atmosphere due to medical use has increased and is likely to increase further. Currently, forty million anaesthetics are delivered per year in the US, and five million are delivered per year in the UK. The majority of these anaesthetics are delivered under the influence of volatile agents. In addition, it is estimated that medical use of $N_2O$ contributes 3% of US $N_2O$ emissions.

An alternative way to capture the agent vapour 14 from the waste gas 38 of the breathing circuit 2 is to subject the waste gas 38 to extreme cold using liquid oxygen. Halocarbons will crystallise at around $-118°$. However, due to safety issues surrounding the use of liquid oxygen and the practicalities of removing and separating crystalline volatile agents from super-cold oxygen pipework, this is not a viable option for most medical establishments.

Another prior art system to capture volatile anaesthetic agent from the waste gas 38 is to pass the waste gas 38 over silicon dioxide ($SiO_2$), also known as "silica" for extraction by steam. An example of this type of prior art system is described in International Patent Application Publication No. WO 2011/026230 A1.

Similarly to the charcoal method described above, the waste gas 38 is captured from the exhaust pipe 40 and passed through canisters that contain granular $SiO_2$ to which the agent 12 binds. Once the $SiO_2$ is saturated with agent 12, the $SiO_2$ canisters are removed for processing. During processing the $SiO_2$ is subjected to a steam purge gas at high pressure and high temperature to separate the agent 12 from the $SiO_2$. Collected anaesthetic agent must be purified to remove water and then separated by fractional distillation.

SUMMARY OF THE INVENTION

Against the above background it is an aim of the present invention to at least provide methods and apparatus for capturing, reclaiming, recycling and using halocarbons which overcome the problems discussed above. These and other uses, features and advantages of the invention will be apparent to those skilled in the art from the teachings provided herein.

According to an aspect of the invention, there is provided a method for capturing halocarbon from a gas. The method may comprise processing gas containing halocarbon with material which is undamaged by exposure to supercritical fluid. Alternatively or in combination, the method may comprise passing gas containing halocarbon through material. The halocarbon may be an anaesthetic agent. Capturing halocarbon may comprise exposing the gas to the material. In preferred embodiments, the method may be performed in a medical environment, wherein the material may be a filter material.

The material may be housed in a module which is resistant to supercritical fluid to enable captured halocarbon to be reclaimed by being dissolvable in a supercritical fluid to form a supercritical solution. Accordingly, the module may be arranged to withstand fluid at supercritical pressure which may be between about 7 MPa and 50 MPa; and/or may be arranged to withstand fluid at supercritical temperature which may be between 30° C. and 100° C. Preferably, the module is arranged to withstand high internal pressure.

The halocarbon may be separated from the supercritical solution. The supercritical solution and/or the separated halocarbon may be delivered as required. These further aspects of the invention are discussed further below. The combination of the aspects of the invention enables halocarbon to be continuously recycled. In a medical environment, the halocarbon may be anaesthetic agent, which may be a volatile anaesthetic agent, and the invention enables the anaesthetic agent to be recycled and reused.

The method preferably comprises passing gas containing one or more halocarbons through material. The material may be or comprise aerogel. The most common aerogel is made of silicon dioxide ($SiO_2$), but aerogels according to the invention may be made from or comprise other materials, for example, resorcinol formaldehyde, carbon, calcium carbonate and zeolite (aluminosilicate). Zeolites are micro-porous alumina silicate minerals found naturally but may also be made artificially. Carbon may be exposed to high temperatures to expand its surface area for absorption. The filter material may be doped with a metal. According to the invention, aerogel may be functionalised by the addition of one or more of halocarbon, metal oxide, cellulose, carbon nanotubes, or internally supported by polymers to improve their chemical or mechanical properties. These changes may improve the binding of halocarbons and/or the stability of the aerogel. For example, functionalisation with halocarbon improves the binding of halocarbon to the material. The material may comprise granular particles.

Furthermore, the material may comprise or be a metal or metal oxide which may be formed by forming metal-oxygen-metal bridges. Examples of preferable metals and metal oxides include nickel oxide, molybdenum oxide, alumina, titania, zirconia, iron oxide, chromia, vandia platinum, rhodium, palladium and tungsten. The material may comprise or be a precious metal. A metal and/or a metal oxide may be added by deposition to the material, for example by physical or chemical vapour phase deposition.

The halocarbon may bind to the material as the gas passes through the material. The material may capture the halocarbon from the gas which may be the waste gas from an anaesthetic machine.

The gas may be processed when the halocarbon in the gas binds to the material. After processing by the material, processed gas may pass through a capture agent to capture halocarbon not processed by the material. The capture agent may be activated charcoal. Gas which has been processed by the material may be monitored for halocarbon. The concentration of the processed gas may be monitored as a concentration of halocarbon in processed gas above a predetermined saturation threshold which may indicate that the material may be saturated with halocarbon. The method may comprise monitoring processed gas for an increase in the concentration of halocarbon in the processed gas, which may indicate that the material is saturated with halocarbon. The method may comprise stopping the supply of gas to the material when the material is saturated with halocarbon. The method may comprise switching the supply of gas so that it is processed by alternative material as described herein. The alternative material may be housed in a further module.

The gas may be from atmospheric air in a medical environment. The gas may be supplied by an anaesthetic machine. The gas may be supplied by a cardiopulmonary bypass machine. Accordingly, a further aspect of the invention extends to a method of capturing anaesthetic agent from a gas, the method comprising passing gas containing anaesthetic agent through filter material.

According to an aspect of the invention there is provided a method for reclaiming, removing or extracting halocarbon from a material. The method may comprise exposing or subjecting the material to a supercritical fluid. A supercritical fluid will expand to fill its container and effuse through solids like a gas and dissolve materials like a liquid.

Subjecting material to which halocarbon is bound to a supercritical fluid breaks the interactions between the halocarbon and the material, and the halocarbon may be displaced from the material and/or dissolves in the supercritical fluid to form a supercritical solution containing the halocarbon. Accordingly, the halocarbon may be bound to or interact with the material so that when the material is exposed to supercritical fluid, the halocarbon may be displaced and dissolves in the supercritical fluid. The material may contain a plurality of different halocarbons which may be reclaimed from the material. The supercritical solution may then carry the halocarbon away from the material leaving the material intact. A supercritical fluid is a substance at a temperature and pressure above its critical point where distinct states of gas or liquid do not exist.

Accordingly, before the material is subjected to supercritical fluid, the halocarbon is preferably bound to the material. The material is arranged to allow the supercritical fluid to pass through the material. The material may be a filter material. The material may comprise an aerogel.

The supercritical fluid may be at a pressure between about 7 MPa and 50 MPa; and may be at a temperature between 30° C. and 100° C. The material is preferably housed in a module which may be resistant to fluids at supercritical temperature and pressure. The module may be arranged to withstand high internal pressure.

The supercritical fluid may be or comprise supercritical carbon dioxide ($CO_2$). Carbon dioxide exists in a supercritical state above its critical temperature (31.1° C.) and critical pressure (7.39 MPa). This temperature is close to room temperature and the pressure is within pressures often used in medicine and in operating theatres. The halocarbon may be one or more anaesthetic agents which are very soluble in supercritical $CO_2$ and may be washed from the material by dissolving in supercritical $CO_2$. Alternatively, the supercritical fluid may be or comprise nitrous oxide ($N_2O$).

In medicine, nitrous oxide may be used alongside anaesthetic agents to maintain anaesthesia. $N_2O$ becomes supercritical at a similar temperature and pressure as $CO_2$. However, $N_2O$ is often unstable when supercritical. Supercritical $N_2O$ may be broken down or reduced by including a reduction catalyst. For example, a metal catalyst reduces nitrous oxide, often in the presence of urea or ammonia. In a preferred embodiment of the invention, the material comprises a reduction catalyst, which may be a metal catalyst which may be deposited on the material. A preferred metal catalyst is platinum. The catalyst may be loaded with reactant, preferably urea, before the halocarbon has been captured by the material or before the material is exposed to supercritical fluid. As gas is exposed to the material nitrous oxide in the gas may react with the urea ($CO(NH_2)_2$) in the presence of the catalyst to form nitrogen ($N_2$), water ($H_2O$) and carbon dioxide ($CO_2$).

In a preferred embodiment of the invention, when the material has been exposed to halocarbon and nitrous oxide, the material may be flushed with supercritical $CO_2$ to elute the halocarbon and remaining nitrous oxide ($N_2O$). Carbon dioxide may be supplied to the material and pressurised to achieve supercritical pressure, preferably around 10 MPa, and heated to achieve supercritical pressure, preferably around 35° C. However, other supercritical temperatures and pressures may be used. When the supercritical $CO_2$ flows through the material the $N_2O$ may be diluted in supercritical $CO_2$ and may become supercritical $N_2O$. The supercritical $N_2O$ and supercritical $CO_2$ mixture may pass through the material, catalyst and/or reactant. The breakdown $N_2O$ of may occur at supercritical temperatures and pressures. At supercritical temperatures and pressures the reaction speed of the breakdown of $N_2O$ is significantly faster than at room temperature and pressure. The invention is advantageous in that, the dilution of $N_2O$ in supercritical $CO_2$ prevents a runaway reaction occurring, which may cause an explosion. Nitrogen gas, water and any other by-products may be separated by the separation steps detailed herein.

Preferably, the material is exposed to supercritical fluid when the material is saturated with halocarbon. When the material is exposed to supercritical fluid it may be flushed with supercritical fluid to elute the halocarbon and any nitrous oxide.

The method may comprise the step of supplying supercritical solution to a separation system for separating halocarbon from the supercritical solution. The supercritical fluid in the supercritical solution may act as a mobile phase. The separation system may comprise at least one chromatography column. The separation system may comprise a fractionating column.

The halocarbon may comprise a plurality of different types of halocarbon, wherein the method may comprise separating one or more of the different types of halocarbon from the supercritical solution. The method may comprise the step of removing non-halocarbon contaminants from the supercritical solution. The method may comprise the step of removing nitrous oxide ($N_2O$) from the supercritical solution.

Prior art methods of reclaiming, removing or extracting halocarbon from material using steam require further steps to separate halocarbon from the steam so that the halocarbon may be reused. Prior art systems and methods typically include a steam purge of the material; separation of halocarbon by condensation separation; and purification of the halocarbon by fractional distillation.

The method of reclaiming halocarbon from filter material according to the invention is advantageous over the prior art in that the supercritical fluid may be used as the separating agent when removing the halocarbon from the supercritical solution. The present invention advantageously combines extraction of the halocarbon from the filter material with separation of the halocarbon from the supercritical solution, as described below. The invention disposes of the need to remove water from the solutions produced by the prior art methods. The present invention advantageously combines one or more of the reclamation of halocarbon from filter material, the separation of halocarbon from supercritical fluid, the purification of halocarbon and the delivery of halocarbon.

In particular, an aerogel may be damaged by steam or purge vapours according to the prior art, which exert surface tension on the delicate structure of the aerogel. Aerogels are not damaged by supercritical $CO_2$ because supercritical $CO_2$ exerts no surface tension.

According to a further aspect of the invention, the invention extends to a module for processing halocarbon. Preferably, the module may comprise material for capturing halocarbon from a gas. In a preferred embodiment, the module is arranged to withstand supercritical fluid. The module may comprise a housing for housing the material. The module, and preferably the housing, may be arranged to allow the gas and supercritical fluid to pass through the material. Preferably, the gas and the supercritical fluid pass through the material alternately. Preferably, the gas and the supercritical fluid pass through the material at alternate times.

The module may be arranged so that the gas and the supercritical fluid may move through the material in opposite directions. Alternatively, the gas and the supercritical fluid may move through the filter material in similar directions. Preferably, the module is arranged to withstand supercritical pressures in the range of between about 7 MPa and 50 MPa. Preferably, the module is arranged to withstand high internal pressure.

As mentioned above, the material may be a filter material, and the material may comprise aerogel. Since the material may be manufactured using a supercritical process, the material may be reusable in a plurality of reclamation cycles. The module may be arranged to allow the material to be replaced. The pore size of the aerogel may range between 0.5 and 50 nm (5 and 500 Angstroms). The material may comprise one or more of silicon dioxide (silica), zeolite (aluminosilicate), carbon and activated carbon. The material, which may preferably be an aerogel, may be doped with metal, cellulose, carbon nanotubes, a polymer or a halocarbon. The material may comprise granular particles. The material may comprise a metal catalyst. The metal catalyst may comprise platinum. The material may comprise a reactant. The reactant may comprise one or more of urea, anhydrous ammonia and aqueous ammonia.

The module may be arranged to allow the ingress and egress of gas containing halocarbon and/or supercritical fluid through the material. Preferably, the module may comprise a first conduit to allow the ingress and egress of gas and supercritical fluid. The module may comprise a second conduit to allow the ingress and egress of gas and supercritical fluid, wherein the first conduit may allow gas to ingress into the module and supercritical fluid to egress the module; and the second conduit may allow gas to egress the module and supercritical fluid to ingress into the module.

The module may comprise a first pair of conduits and may comprise a second pair of conduits. Either or both pairs of conduits may be arranged to allow the ingress and egress of fluid through the filter material. Preferably, the first pair of conduits may allow the ingress and egress of gas, and the second pair of conduits may be arranged to allow the ingress and egress of supercritical fluid.

The module may comprise an air intake duct arranged to allow atmospheric air to be processed by the material. The module may be arranged to allow atmospheric air to pass through the filter material. In a preferred embodiment, the module is a canister.

According to another aspect, the invention extends to a halocarbon recycling system comprising at least one module as described above.

If the invention is used in a medical environment, an air intake duct may allow the entrainment of air from the local environment in order to capture escaped anaesthetic agent gas from an operating theatre, which may be in addition to receiving gas from a medical device, such as the exhaust of an anaesthetic machine. In an alternative embodiment, the module may be arranged to allow the ingress and egress of gas containing anaesthetic agent through the filter material via one pair of conduits, and the ingress and egress of supercritical fluid through the filter material via the other pair of conduits. According to a further aspect of the invention, there is a module for recycling anaesthetic agent from a gas, the module comprising a housing comprising filter material for capturing anaesthetic agent from a gas, wherein the housing is arranged to allow supercritical fluid to pass through the filter material.

According to another aspect of the invention there is provided a medical device comprising at least one module as described above. Preferably, the medical device comprises a plurality of modules, and the anaesthetic machine is arranged to concurrently supply (i) gas containing anaesthetic agent to at least one of the modules of the plurality of modules; and (ii) supply supercritical fluid to at least one other of the modules of the plurality of modules. In a preferred embodiment, the anaesthetic machine may be arranged to switch the supply of gas and supercritical fluid between the modules of the plurality of modules to enable a continuous flow of anaesthetic.

According to an aspect of the invention there is provided a processing method for separating one or more substances from a supercritical solution. The method preferably comprises separating one or more halocarbons from a supercritical solution comprising halocarbon and supercritical fluid. Preferably, the one or more halocarbons may be dissolved in the supercritical fluid. The method may comprise supplying the supercritical solution to a separation system.

The method may comprise using supercritical fluid as the mobile phase in the separation system which may be an elution system. The separation method may be used to purify and collect the one or more halocarbons from the supercritical fluid. The method may comprise supplying supercritical fluid to the separation system. The method may comprise producing a product which is monitored for one or more halocarbons. The method may comprise collecting the product if the product contains one or more halocarbons. The method may comprise disposing of the product if the product does not contain halocarbon. The method may comprise the step of removing one or more halocarbons from the product. The method may comprise the step of collecting halocarbon separated from the supercritical fluid. The method may comprise using a cyclonic collector to collect the halocarbon. The method may comprise the step of separating contaminants from the supercritical solution. Preferably, the contaminants comprise of one or more of water, urea, ammonia and formaldehyde.

One or more of the separating steps may be performed by chromatography. Supercritical chromatography may be used after agent has been eluted from capture material. The method of chromatography may be based on polarity, molecular size, molecular weight or other molecular physiochemical differences that lead to different rates of flow under the influence of a supercritical fluid mobile phase. The separating system may comprise monitoring means for monitoring the output from the at least one chromatography column. The system may comprise a controller for controlling the output of the at least one chromatography column. Following depressurisation of the supercritical $CO_2$, one or more temperature controlled cyclonic collectors may collect purified halocarbon or contaminates from the gaseous $CO_2$.

In a preferred embodiment, polarity based normal-phase chromatography columns are used to separate anaesthetic agents (which all have similar polarity) from other contaminants (water, urea, ammonia, formaldehyde, etc.). Different chromatography columns may be used in series to aid separation and more than one column may be required to remove all contaminants. In the preferred embodiment, a molecular size exclusion chromatography column that distinguishes between the molecular sizes of the anaesthetic agents may be used to separate agents from each other for subsequent collection from $CO_2$ in cooled cyclonic collectors.

One or more of the separating steps may be performed by fractionation. Fractionation may be driven by supercritical carbon dioxide. Supercritical fractionation may comprise the separation of volatile fractions of halocarbon dissolved in supercritical fluid by their volatility at different pressures and temperatures. A $CO_2$ mobile phase may be produced by a stepwise reduction in pressure of $CO_2$ from its supercritical pressure to atmospheric pressure. At each pressure stage the mixture may be passed through fractionating columns under temperature control. Accordingly, individual halocarbon fractions may be liquefied for collection. Thus highly purified halocarbon fractions are separated from each other dud from $CO_2$.

In the aspects described above, the one or more halocarbons may be one or more anaesthetic agents. The one or more anaesthetic agents may be one or more volatile anaesthetic agents. The one or more halocarbons may also be industrial halocarbons used or produced by industrial processes.

In order to retrieve one or more substances from a supercritical fluid, an aspect of the invention extends to a separation system for retrieving one or more substances from a supercritical solution, wherein the separation system is arranged to separate halocarbon from a supercritical solution comprising halocarbon and supercritical fluid.

The separating system may comprise separating means to which supercritical solution may be supplied. The separating means may comprise at least one chromatography column into which supercritical solution may be supplied. The separating means may comprise at least one fractionation column into which supercritical solution may be supplied. The separating system may comprise monitoring means for monitoring the product produced by the separating means. The monitoring means may comprise an infrared spectroscopy sensor. The infrared spectroscopy sensor may be a Fourier transform infrared spectroscopy device. Alternative monitoring means and methods include mass spectroscopy, UV detection, Raman spectroscopy, Acoustic resonance spectroscopy and piezoelectric crystal resonance.

Preferably, the system may comprise a controller for controlling the output of the separating means, wherein the controller may direct the output of the separating means to a collection module if the product contains halocarbon. The collection module may be arranged to separate one or more of the halocarbon types. The system may comprise a collection module control means for controlling the input of product into the collection module. The system may comprise a collection module monitoring means for monitoring the halocarbon type entering the collection module. The collection module monitoring means may comprise an infrared spectroscopy sensor. The infrared spectroscopy sensor may be a Fourier transform infrared spectroscopy device. The collection module may comprise at least one cyclonic collector.

When the invention is used in a medical environment, the halocarbon may be an anaesthetic agent. Accordingly, the invention extends to a method of delivering or introducing anaesthetic agent to a medical device. Preferably, the anaesthetic agent is dissolved in a supercritical fluid. According a preferred embodiment of the invention, the supercritical fluid containing the anaesthetic agent is injected into the inspiratory limb of an anaesthesia breathing circuit.

An anaesthetic machine according to the prior art mixes oxygen/air/nitrous with anaesthetic agent and then delivers it to the breathing circuit. The present invention is advantageous in that it is necessary to only add oxygen and/or air to a breathing circuit to replace those gasses that a patient consumes during anaesthesia. This is typically approximately 200 ml/min oxygen. According to the present invention, anaesthetic agent which is dissolved in supercritical fluid may be added directly into the breathing circuit, i.e. independently of the oxygen and/or air.

In the prior art, if a clinician wishes to give a patient more anaesthetic they must deliver more oxygen/air/nitrous through the vaporiser and into the breathing circuit. This displaces some of the gas being recirculated in the breathing circuit of an anaesthetic machine, which wastes the displaced gas. The invention is advantageous in that the flow of gas does not have to be altered to alter the concentration of anaesthetic agent delivered to the patient. The flow of oxygen/air/nitrous may be continuous and steady and does not alter depending on the concentration of agent that is required. Preferably, a control module, such as a computer, may calculate the amount of anaesthetic agent to be delivered directly into the breathing circuit based on the concentration the clinician requires. Accordingly, the clinician may change the desired anaesthetic agent concentration without altering the flow of oxygen/air/nitrous. For example, when a clinician wishes to increase the depth of anaesthesia of a patient, the clinician may increase the concentration of anaesthetic supplied to the breathing circuit. Conversely, when the clinician wishes to revive the patient, the clinician may selects an anaesthetic concentration of zero which results in anaesthetic agent being captured and/or reclaimed from the breathing circuit. The gas in the breathing circuit may therefore be replaced with fresh oxygen/air/nitrous.

Therefore, in a preferred embodiment, the medical device may be an anaesthetic machine, and the supercritical fluid containing the anaesthetic agent may be delivered to the anaesthetic machine. Preferably, anaesthetic agent may be injected into the medical device. The supercritical fluid containing the anaesthetic agent may be delivered or injected into the backbar or breathing circuit of the anaesthetic machine.

The medical device may be a cardiopulmonary bypass machine. The supercritical fluid containing the anaesthetic agent may be delivered to the cardiopulmonary bypass machine. The supercritical fluid containing the anaesthetic agent may be delivered to the gas flow to the oxygenator of the cardiopulmonary bypass machine. The supercritical fluid containing the anaesthetic agent may be injected into the arterial line of the cardiopulmonary bypass machine.

The method may comprise capturing anaesthetic agent from a medical device. The method may comprise monitoring the level and/or concentration of anaesthetic agent entering and or exiting the medical device. The method may comprise adjusting delivery of anaesthetic agent by computer and/or by clinician control.

Accordingly, an aspect of the invention also extends to a system for delivering or introducing anaesthetic agent to a medical device. Preferably, a supercritical solution of anaesthetic agent may be dissolved in supercritical fluid and delivered to a medical device. The system may comprise a cartridge or storage tank containing the supercritical solution of anaesthetic agent dissolved in supercritical fluid.

Preferably, the system comprises delivery means for delivering the supercritical solution to the medical device. The delivery means may comprise an injector for delivering the supercritical solution. The delivery means may comprise a warming sleeve to maintain a supercritical temperature. The system may be arranged to deliver the supercritical solution to an anaesthetic machine or a cardiopulmonary bypass machine. The system may be arranged to introduce anaesthetic agent into the breathing circuit of the anaesthetic machine or into the cardiopulmonary bypass machine.

The system may comprise at least one sensor for monitoring the level of anaesthetic agent in the system. Preferably, the at least one sensor may comprise an infrared spectroscopy sensor. The infrared spectroscopy sensor may be a Fourier transform infrared spectroscopy device. The system may comprise a control module for controlling the amount of anaesthetic agent delivered by the system. The system may comprise an injector module or an injector. The injector module or the injector may be arranged to deliver anaesthetic agent and supercritical fluid to the breathing circuit or backbar of the anaesthetic machine, or the arterial line of a cardiopulmonary bypass machine. The system may comprise a control module for controlling the amount of anaesthetic agent delivered by the system.

The injector may be computer-controlled to enable the delivery of precise amounts of diluted halocarbon into the breathing circuit using the pressure of the supercritical fluid as the driving pressure. The injector may be warmed to prevent icing as the supercritical fluid is depressurised. As the supercritical fluid is warmed and depressurises, it disperses and vaporises the halocarbon for delivery to the patient. The carbon dioxide absorber in the breathing circuit may absorb the small amounts of carbon dioxide used to deliver the agent.

The delivery system may include one or more modules as described above and/or the recycling system as described above. The system may comprise a pressurised and temperature-regulated module containing halocarbon dissolved in supercritical fluid.

It will be clear to those skilled in the art that the delivery system can be used in combination with the capture, reclamation and separation systems above to provide a mobile, closed-loop anaesthetic machine that is able to deliver and recycle anaesthetic gases.

According to another aspect of the invention there is provided a method and system for recycling halocarbon. In addition to the preferred embodiments below, the method and system for recycling halocarbon may comprise any combination of the capturing, reclamation, separation and delivery steps and apparatus described above.

The method for recycling halocarbon preferably comprises processing gas containing halocarbon with halocarbon-binding material to bind halocarbon to the material; and may comprise exposing the material to supercritical fluid to dissolve halocarbon bound to the material in the supercritical fluid to form a supercritical solution.

Preferably, the gas is processed by passing the gas through the material. The supercritical fluid may pass through the material to dissolve halocarbon bound to the material. The method may comprise monitoring the concentration of halocarbon in the processed gas, and may comprise switching from the processing step to the exposing step at a predetermined concentration of halocarbon. Preferably, the method may alternate between the processing and exposing steps. Alternatively, the processing steps and exposing steps may take place concurrently.

In a preferred embodiment, the method may comprise the step of separating halocarbon from the supercritical solution. The method may comprise delivering supercritical solution to a medical device. Preferably, the gas containing halocarbon may be provided by a medical device. The method may comprise monitoring the concentration of halocarbon delivered to the device, and may comprise monitoring the concentration of halocarbon received from the medical device.

According to an aspect of the invention there is provided a recycling system for recycling halocarbon. The recycling system preferably comprises halocarbon-binding material for capturing halocarbon from a gas. The system may be arranged to expose material (i) to gas containing halocarbon to capture the halocarbon; and preferably (ii) to supercritical fluid to dissolve the halocarbon in a supercritical solution.

The recycling system may comprise at least one module as described above. The recycling system may comprise a gas ingress pipe for supplying gas containing halocarbon to at least one module. The recycling system may comprise a gas egress pipe for carrying processed gas away from at least one module. The recycling system may comprise a supercritical fluid ingress pipe for supplying supercritical fluid to at least one module. The system may comprise a supercritical fluid egress pipe for carrying supercritical fluid in which halocarbon is dissolved away from the module.

Accordingly, material may be housed in one or more modules. The recycling system may be arranged to supply fluid to one or more of the modules so that the supercritical fluid passes through the material to dissolve halocarbon. In a preferred embodiment, the fluid is supercritical fluid. In a preferred embodiment, the fluid is gas. The gas preferably contains halocarbon. The recycling system may be arranged to supply gas containing halocarbon to one or more modules so that gas passes through the material to capture halocarbon.

The system may be arranged to switch between exposing the material to gas containing halocarbon to capture the halocarbon, and exposing the material to supercritical fluid to dissolve the halocarbon. The system may be arranged to alternately expose the material to (i) gas containing halocarbon; and (ii) supercritical fluid. The system may be arranged to expose material to gas containing halocarbon; and to expose material to supercritical fluid at the same time.

The system may be arranged so that each module of a plurality of modules may be arranged to expose the material housed in the module to (i) gas containing halocarbon to capture the halocarbon; and (ii) supercritical fluid to dissolve the halocarbon in a supercritical solution. Each module of the plurality of modules may be arranged to switch between exposing the material housed in the module to (i) gas containing halocarbon to capture the halocarbon; and (ii) supercritical fluid to dissolve the halocarbon in a supercritical solution.

The system may be arranged to supply gas to one or more modules of the plurality of modules to capture halocarbon at the same time as supercritical fluid passes through at least one of the other modules to dissolve halocarbon. The system may be arranged to switch the modes of one or more of the modules of the plurality of modules between exposing the material (i) to gas containing halocarbon to capture the halocarbon; and (ii) to supercritical fluid to dissolve the halocarbon in a supercritical solution.

In an embodiment of the recycling system which has at least two modules, the system may be arranged to pass gas containing halocarbon through one module to capture the halocarbon, and pass supercritical fluid though the other module to dissolve captured halocarbon. In a preferred embodiment, the system is arranged to switch a first module from passing gas containing anaesthetic agent to passing supercritical fluid through the first module; and switch a second module from passing supercritical fluid to passing gas containing anaesthetic agent. This enables the system to switch operation when or before the module through which gas containing anaesthetic agent passes is saturated with halocarbon.

The recycling system may comprise a gas ingress means for supplying gas containing halocarbon to the material. The system may comprise control means for controlling the flow of gas to the material. The system may comprise a gas egress means for carrying processed gas away from the material. The recycling system may comprise monitoring means for monitoring the concentration of halocarbon in the processed gas, and the monitoring means may be arranged to send a control signal to the control means. The recycling system may comprise a supercritical fluid ingress pipe for supplying supercritical fluid to the material. The system may comprise a supercritical fluid egress pipe for carrying supercritical fluid in which halocarbon may be dissolved away from the material.

Advantageously, the invention enables a continuous flow of gas containing halocarbon to be processed while, preferably at the same time, a continuous flow of halocarbon dissolved in supercritical fluid may be provided for use. In an embodiment where the halocarbon contains one or more anaesthetic agents, the invention enables anaesthetic agent returning from a patient under anaesthesia to be captured from a gas, reclaimed from the material and delivered back to the patient. Therefore, in a preferred embodiment, the recycling system may deliver the supercritical solution to a medical device. The gas may contain halocarbon which may be supplied from a medical device.

Accordingly, the invention enables halocarbon to be constantly captured from waste gas without interruption; and halocarbon, which may be one or more anaesthetic agents, may be continuously provided to apparatus for inducing anaesthesia. For example, an anaesthetic machine. Alternatively, the invention may provide halocarbon to a cardiopulmonary bypass machine. Accordingly, the recycling system may be arranged so that gas passes through one module to capture halocarbon at the same time as supercritical fluid passes through another module to dissolve halocarbon captured by the other module.

The operation of each module in a plurality of modules may be switched, and the switch may be synchronised between each module so that each model switches operation at the same time, so that the system may be arranged to switch the operation of the modules concurrently.

Preferably, the recycling system comprises gas control means to switch the flow of gas between the modules. The system may comprise a further gas ingress pipe for supplying gas containing halocarbon to a further module. The system may further comprise a further gas egress pipe for carrying processed gas away from the further module.

In a preferred embodiment, the recycling system comprises monitoring means arranged to monitor the concentration of halocarbon egressing from each module. Preferably, the monitoring means is a Fourier transform infrared spectroscopy (FT-IR) device. The system may comprise gas flow control means to control the flow of gas to the modules.

Preferably, the monitoring means is arranged to send a signal to the gas control means to switch the gas flow between the modules when the monitoring means detects that one of the modules is saturated with halocarbon. This allows the modules to be swapped when the module processing the gas reaches saturation point, thereby providing a continuous flow of useable halocarbon.

In a preferred embodiment, a supercritical solution of anaesthetic agent may be injected into the gas stream supplying the oxygenator, or injection into the oxygenator gas flow, of a cardiopulmonary bypass machine. This enables diffusion of volatile anaesthetic agent to equal partial pressures from the gas into blood passing through the oxygenator to maintain anaesthesia. Halocarbon that does not dissolve and gas that has transferred from blood into the oxygenator down any partial pressure gradient is exhausted. In one embodiment of the invention, exhaust gases from the oxygenator are passed through a module to capture halocarbon.

The delivery system may comprise a pressurised and temperature-regulated module containing anaesthetic agent dissolved in supercritical fluid and a warmed injector module to deliver exact amounts of anaesthetic agent and supercritical fluid to either the gas passing to the oxygenator or directly into the arterial blood supply. In the case of delivery to the oxygenator gas supply, the warming and depressurisation of the supercritical fluid drives dispersion and/or vapourisation of anaesthetic agent into the gas stream. In the case of delivery to the arterial tube of the cardiopulmonary bypass machine, carbon dioxide quickly dissolves in blood due to its high solubility, which quickly dilutes anaesthetic agent into the blood.

Advantageously, the invention provides a closed recycling system that enables the safe delivery of accurate concentrations of volatile agents to patients without the need ventilation of a patient in cardiac anaesthesia. Currently, if volatile agents are used to supply the oxygenator from a conventional vapouriser, high flows are required and are wasteful. Many hospitals therefore use intravenous anaesthesia during cardiopulmonary bypass. This invention enables the efficient use of volatile anaesthetic agents, which is advantageous as they are reported to have better neuroprotective effects than propofol.

Furthermore, pure volatile anaesthetic agent is extremely insoluble in water or blood. Therefore, anaesthetic agent may remain as a bolus in the patient's circulation when delivered directly into a patient's blood as a liquid. The invention therefore overcomes the problem of how to provide a system for providing volatile anaesthetic agent directly into blood at a concentration low enough to be safe.

It will be clear to those skilled in the art that the module and delivery system may be used separately. The capture module may be used to recycle anaesthetic gases delivered before and/or during cardiopulmonary bypass by a conventional anaesthetic machine, in which a vaporiser supplies an oxygenator. A separate stand-alone source of anaesthetic agent dissolved in supercritical fluid may be used for delivery of anaesthetic agent dissolved in supercritical fluid to a medical device. In this way, the delivery system may supply anaesthetic agent independent of a closed-loop system by using a stand-alone source of pressurised, temperature-controlled anaesthetic agent dissolved in supercritical fluid with an injector module.

The system may also comprise a control module for controlling the amount of halocarbon delivered by the system. The control module and/or one or more of the sensors may be linked so that a change in the level of halocarbon returning to the system results in a change in the level of halocarbon delivered by the system. The control module and one or more of the sensors may be linked to maintain a constant supply of halocarbon dissolved in supercritical fluid. This supply would be from recycled halocarbon with system losses replaced either from a liquid source of halocarbon or a separate supply of halocarbon dissolved in supercritical fluid.

The invention provides apparatus and methods of capturing, reclaiming, separating, delivering and recycling halocarbon from waste gas, which may be from the breathing circuit of an anaesthetic machine. By capturing halocarbon, which may comprise, volatile anaesthetic agents, and preventing their release into the atmosphere global halocarbon emissions may be reduced.

The aspects of the invention are interrelated to provide apparatus and methods which improve the capture and reuse of halocarbons in the medical and industrial sectors.

It is to be appreciated that one or more of the aspects, embodiments and features of any of the above aspects or embodiments of the invention may be readily combined, as will be readily apparent to the skilled person. Furthermore, the forgoing advantages may relate to more than one aspect of the present invention.

BRIEF DESCRIPTION OF THE DRAWINGS

Embodiments of the present invention will now be described, by way of example only, with reference to the accompanying drawings, in which like components are assigned like numerals, and in which: —

DETAILED DESCRIPTION

Figure 1:
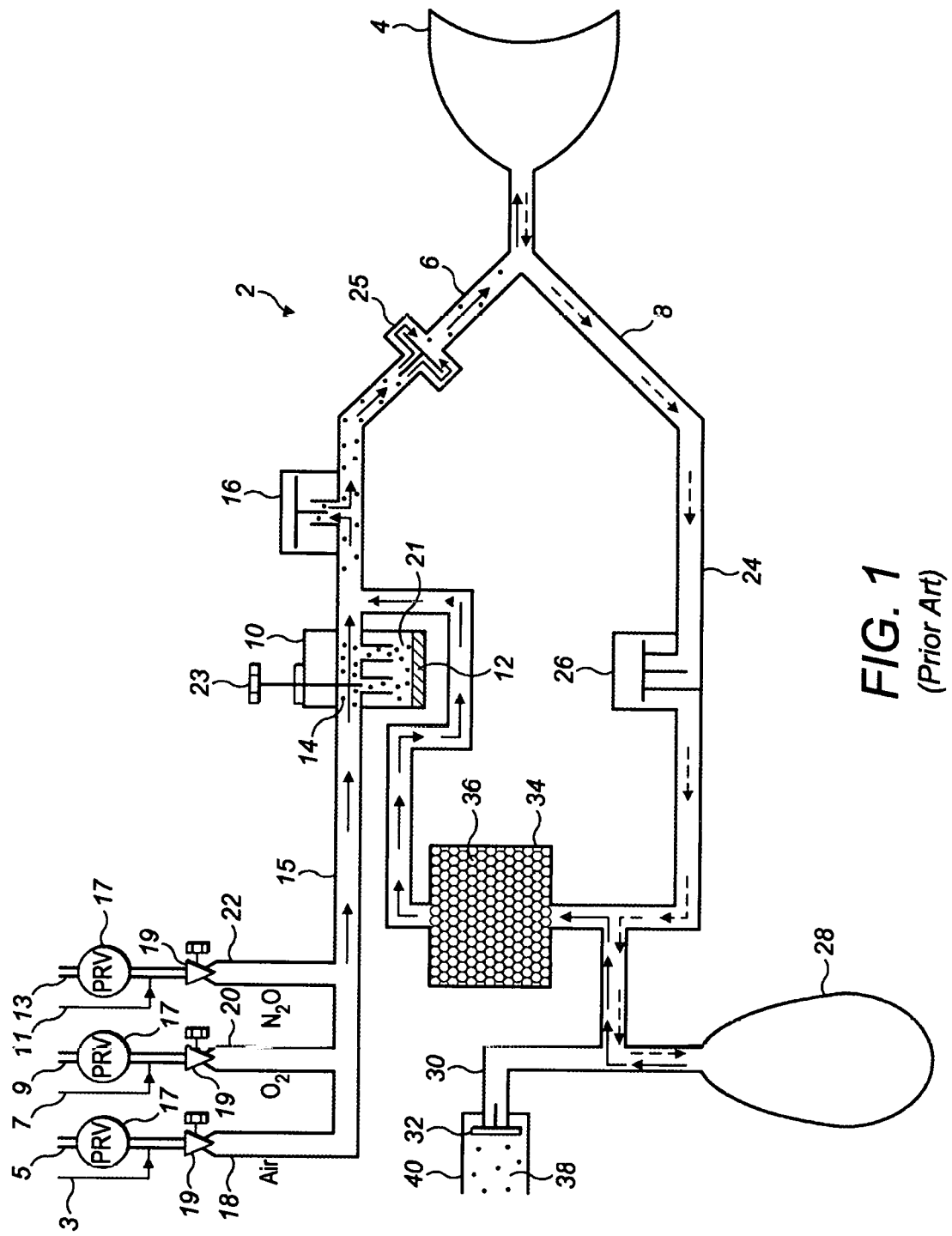
FIG. 1 is a schematic diagram of the breathing circuit of an anaesthetic machine according to the prior art.
Figure 2:
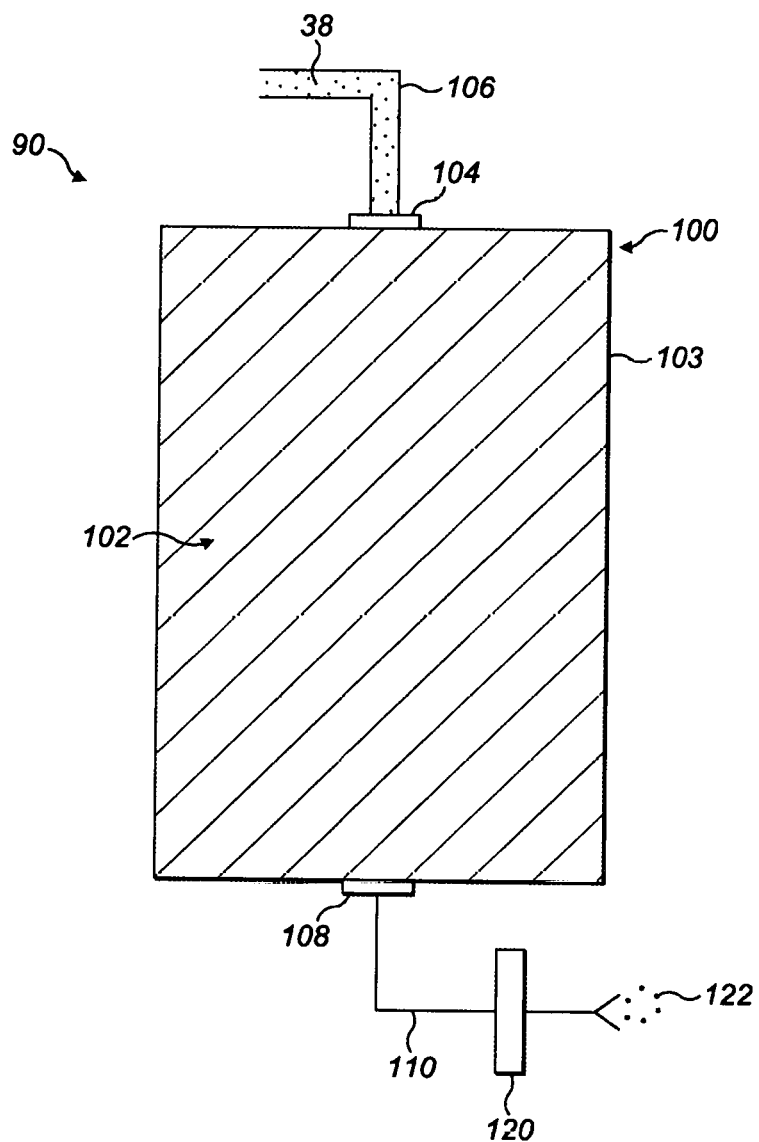
FIG. 2 is a schematic diagram illustrating a module for capturing anaesthetic agent from contaminated gas according to an embodiment of the invention.

A module 90 for processing halocarbon, in particular capturing anaesthetic agent from a gas is shown in FIG. 2. A pressure canister 100 comprises a housing 103 containing material for capturing halocarbon from a gas, which is held in the canister 100 by at least one mesh (not shown in FIG. 2). In the presently described embodiment of the invention the material is a filter material 102 which is an aerogel which is formed from silica ($SiO_2$) and functionalised with halocarbon. In alternative embodiments of the invention the filter material may comprised from other materials described below. The module 90, and in particular, the canister 100, is able to withstand supercritical fluid to allow supercritical fluid to pass through the filter material 102.

An aerogel is a synthetic porous ultra-light material derived from a gel, in which the liquid component of the gel has been replaced with gas. An aerogel is formed by first creating a gel. Once the gel is created, the liquid component of the gel is removed by solvent exchange. Finally, the material is subjected to supercritical $CO_2$. Supercritical $CO_2$ is a fluid state of $CO_2$ in which $CO_2$ is at a pressure and temperature at or above its critical temperature and pressure, which are 31.1° C. (304.25 K) and 7.39 MPa (72.9 atm) respectively. When it is in a supercritical state, $CO_2$ has the properties of a gas and a fluid in that it will expand to fill its container like a gas but can dissolve materials like a liquid. In addition, supercritical $CO_2$ does not have any surface tension. Therefore, when supercritical $CO_2$ is allowed to vaporise it does not exert capillary hydrostatic pressures onto the aerogel material that would normally collapse it. The end result is that all the liquid is removed from the gel to arrive at an aerogel in which the gel structure remains intact.

The most common type of aerogel is silica aerogel. However, other aerogels exist, such as aerogels manufactured from carbon or metal oxides, calcium carbonate and resorcinol formaldehyde. The produced aerogel may be doped with metal compounds, such as nickel, precious metals, fluorocarbons or metal oxides. Doping of the aerogel gives certain properties such as preventing water absorption, gas selectivity, catalysis or adsorbent characteristics, for example. The produced aerogel may also be functionalized by cellulose, carbonisation of the aerogel, carbon nanotubes and polymerisation of monomer after aerogel formation to improve mechanical strength.

The canister 100 has an ingress conduit 104 which is removably connected to an ingress pipe 106 which receives waste gas 38 from the exhaust pipe 40 of an anaesthetic machine. As the patient breathes out, the pressure of their exhaled air pushes the waste gas 38 through the pressure release valve 32, which then flows through the canister 100. The canister 100 comprises an egress conduit 108 to which an egress pipe 110 is removably connected. Processed gas 122 exits the canister 100 through the egress pipe 110 into the atmosphere. The egress pipe 110 comprises a small activated charcoal filter 120 through which gas exiting the canister 100 passes to ensure that any residual volatile agent is absorbed and prevented from being released into the atmosphere.

In use, waste gas 38 flows from the exhaust pipe 40 of the anaesthetic machine into the ingress pipe 106. The anaesthetic machine from which the canister 100 receives waste gas 38 may deliver several different types of agent. Accordingly, the canister 100 may process and collect a mixture of volatile anaesthetic agents.

As mentioned above, the waste gas 38 contains non-metabolised volatile anaesthetic agent 12, which is a class of halocarbon. The anaesthetic agent 12 is captured from the waste gas 38 by processing the waste gas 38 containing the anaesthetic agent 12 with the filter material which, as described above, is undamaged by exposure to supercritical fluid. The waste gas 12 containing anaesthetic agent is passed through the filter material 102. The volatile anaesthetic agent 12 in the waste gas 38 binds to the filter material 102 as the waste gas 38 passes through the canister 100. The agent 12 binds to the filter material 102 mainly due to van der Waals and some very week hydrogen bonding. Once the waste gas 38 has passed through the filter material 102, the processed gas 122 exits the canister 100 via the egress pipe 110. Any residual agent 12 remaining in the processed gas 122 is absorbed by the activated charcoal filter 120 before the processed gas 122 exits into the atmosphere.

When the filter material 102 in the canister 100 is saturated with agent 12, the feed of waste gas 38 to the ingress pipe 106 may be terminated and the canister 100 removed from the ingress pipe 106 and the egress pipe 110.

Figure 3:
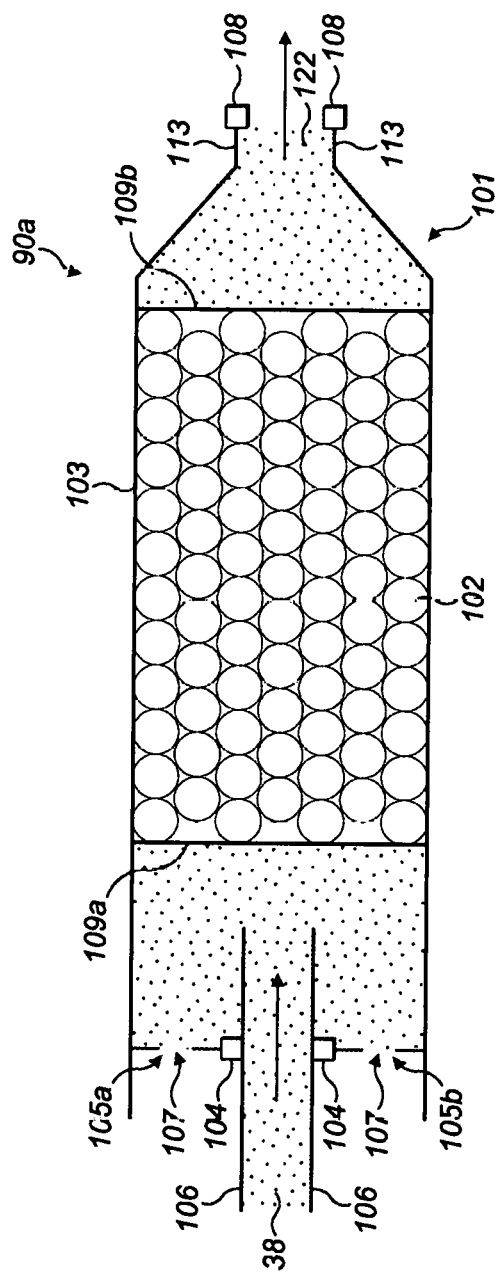
FIG. 3 is a schematic diagram illustrating an alternative module for capturing anaesthetic agent from contaminated gas from the anaesthetic machine and theatre environment according to an embodiment of the invention.

An alternative module 90a according to an alternative embodiment of the invention is illustrated in FIG. 3. A canister 101 has an ingress conduit 104 which is removably connected to an ingress pipe 106 which receives waste gas 38 from the exhaust pipe 40 of an anaesthetic machine. In addition, canister 101 has a first duct 105a and a second duct 105b in the housing 103. The first and second ducts 105a, 105b allow gas from another source to pass through the canister 101. In the presently described embodiment, environmental air 107 from an operating theatre, which may contain small quantities of anaesthetic agent 12, is free to pass through the ducts 105a, 105b.

Filter material 102 is held inside the housing 103 by an ingress mesh 109a and an egress mesh 109b. The meshes 109a, 109b are metal. The canister 101 comprises an egress conduit 108. The width of the canister 101 reduces to form a conical venturi chamber 111 which has an egress neck portion 113. The egress conduit 108 is mounted on the egress neck portion 113.

A pump (not shown) is attached to the egress conduit 108 and arranged to suck the waste gas 38 and environmental air 107 from the ingress pipe 106 and ducts 105a, 105b respectively. The combination of waste gas 38 and environmental air 107 is sucked through the filter material 102. The anaesthetic agent 12 is captured from the combination of waste gas 38 and environmental air 107 as they pass through the filter material 102. The resultant processed gas 122 is then released into the atmosphere after passing through a further activated charcoal filter (not shown in FIG. 3) to capture any residual agent 12.

When the filter material 102 in the canister 101 is saturated with agent 12, the feed of waste gas 38 and environmental air 107 to the canister 101 is terminated and the canister 101 is removed from the ingress pipe 106 and the egress pipe 110.

Figure 4:
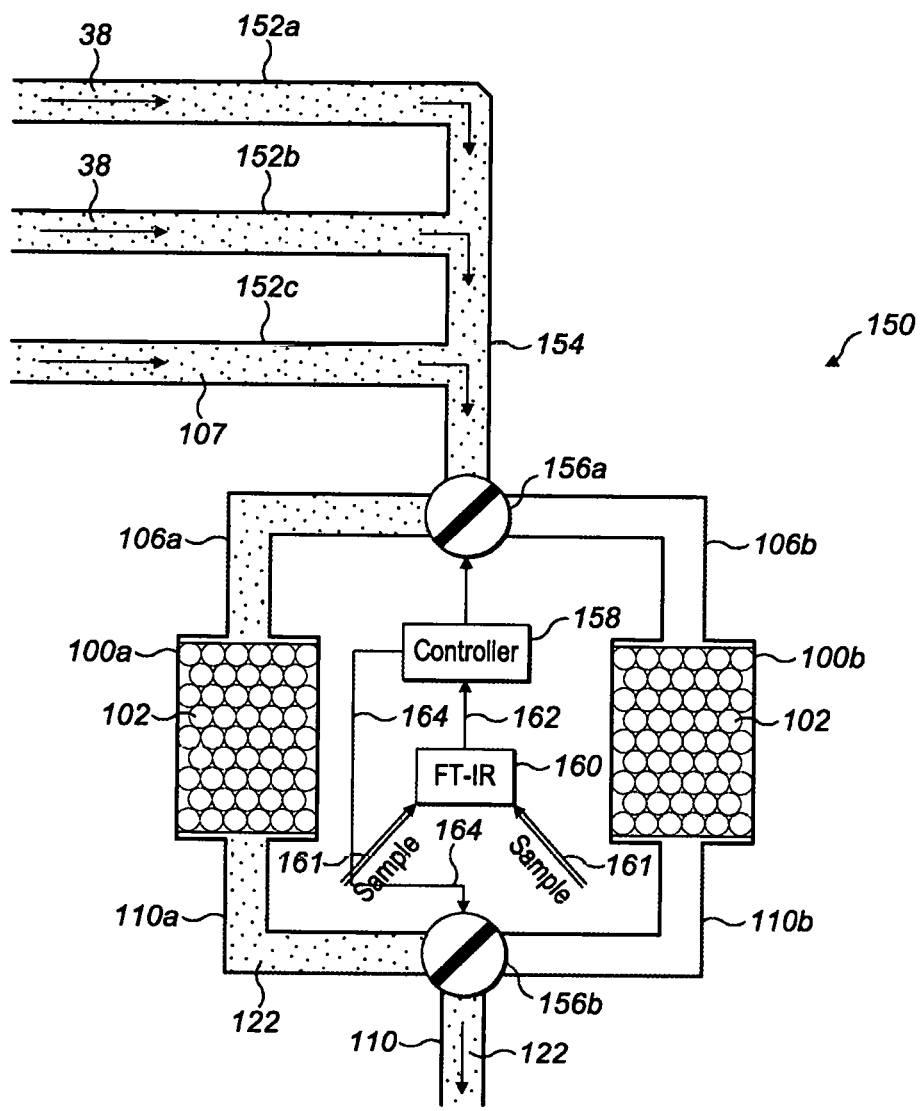
FIG. 4 is a schematic diagram illustrating the invention in use in a medical environment which comprises multiple theatres and/or anaesthetic machines according to an embodiment of the invention.

One or more canisters 100 may be used to process gasses from a plurality of anaesthetic machines and/or operating theatres. FIG. 4 illustrates a processing system 150 for processing gas form a plurality of anaesthetic machines and/or operating theatres using a first canister 100a and a second canister 100b. The canisters 100a, 100b may be similar to the canister 100 described with reference to FIG. 2.

In the system illustrated in FIG. 4, a first receiving pipe 152a receives waste gas 38 from a first anaesthetic machine; a second receiving pipe 152b receives waste gas 38 from a second anaesthetic machine; and a third receiving pipe 152c receives environmental air 107 from an operating theatre. For simplicity three receiving pipes 152a, 152b, 152c are shown in FIG. 4. However, the processing system 150 may comprise any number of receiving pipes. Each receiving pipe 152a, 152b, 152c may receive waste gas 38 from an anaesthetic machine or environmental air 107 from an operating theatre.

The receiving pipes 152a, 152b, 152c converge into a main receiving pipe 154. The waste gas 38 and environmental air 107 flow towards a first directional valve 156a. The first directional valve 156a directs the flow of waste gas 38 and environmental air 107 to either a first ingress pipe 106a or a second ingress pipe 106b. FIG. 4 shows the first directional valve 156a directing the flow of waste gas 38 and environmental air 107 into the first ingress pipe 106a. The first canister 100a is connected between the first ingress pipe 106a and a first egress pipe 110a, so that the waste gas 38 and environmental air 107 flows through filter material 102 in the first canister 100a, which captures anaesthetic agent from the gas 38 and air 107. The second canister 100b is connected between the second ingress pipe 106b and a second egress pipe 110b, so that the waste gas 38 and environmental air 107 flows through filter material 102 in the second canister 100b when the first directional valve 156a directs the flow of gas 38 and air 107 through the second ingress pipe 106b.

The first egress pipe 110a and second egress pipe 110b meet at a second directional valve 156b which directs processed gas 122 to a main egress pipe 110. The second directional valve 156b directs the flow of processed gas 122 from the first egress pipe 110a or the second egress pipe 110b to the main egress pipe 110.

The directions of each of the first directional valve 156a and the second directional valve 156b are controlled by a valve controller 158. The valve controller 158 is operatively linked to a module for monitoring gas. In the present embodiment, infra-red spectroscopy, which in the presently described embodiment is a Fourier transform infrared spectroscopy (FT-IR) device 160, is used to analyse the gas flowing in each of the first and second egress pipes 110a, 110b. In alternative embodiments of the invention, a dispersive infra-red device may be used. The FT-IR device 160 is arranged to receive samples 161 from the gas flowing in each of the first and second egress pipes 110a, 110b. Alternative monitoring means or sensors and methods include mass spectroscopy, UV detection, Raman spectroscopy, Acoustic resonance spectroscopy and piezoelectric crystal resonance.

In the configuration illustrated in FIG. 4, the FT-IR device 160 periodically tests processed gas 122 from the first egress pipe 110a. The FT-IR device 160 analyses each sample for anaesthetic agent 12. Detection of anaesthetic agent 12 above a predetermined concentration in the processed gas 122 indicates that the filter material 102 in the first canister 100a is saturated with anaesthetic agent 12. For example, once the filter material is saturated with agent 12, the concentration of agent 12 in the gas exiting the canister 100a will rise to the concentration of agent 12 entering the canister 100a. If the concentration of agent 12 in the gas exiting the canister 100a and flowing through the first egress pipe 100a, is detected by the FT-IR device 160 as rising above the predetermined threshold concentration, the FT-IR device 160 sends a saturation signal 162 to the valve controller 158.

Alternatively, an increase in concentration of agent 12 exiting the canister 100a may trigger the sending of a saturation signal 162 to the valve controller. For example, while agent 12 is captured by the filter material 102, a constant concentration of agent 12, which may be a trace amount, may exit a canister 100a. Therefore, an indication of saturation of filter material 102 may be the increase in the concentration of agent 12 exiting the canister 100a.

When anaesthetic agent 12 above the predetermined concentration is detected in the first egress pipe 110a by the FT-IR device 160, the FT-IR device 160 sends a saturation signal 162 to the valve controller 158. On receipt of the saturation signal 162 the valve controller 158 sends a switch signal 164 to each of the valve controllers 156a, 156b. On receipt of the switch signal 164 the first valve controller 156a switches the direction of flow of waste gas 38 and environmental air 107 to the second ingress pipe 106b, and the second directional valve 156b switches direction to allow processed gas 122 to flow from the second egress pipe 110b to the main egress pipe 110. Once the gas 38 and air 107 are flowing through the second canister 100b the first canister may be replaced. In turn, once the filter material of the second canister 100b has been saturated the directional valves will switch in the opposite direction to allow the replacement of the second canister 100b.

Accordingly, the processing system 150 provides a system in which the output of more than one anaesthetic machine and/or the environmental air of more than one operating theatre can be passed through a bank of canisters. Further embodiments of the processing system may comprise more than two canisters connected in parallel via corresponding ingress and egress pipes. A processing system according to these further embodiments may be used to process the anaesthetic gas scavenging system (AGSS) of an entire hospital.

Figure 5:
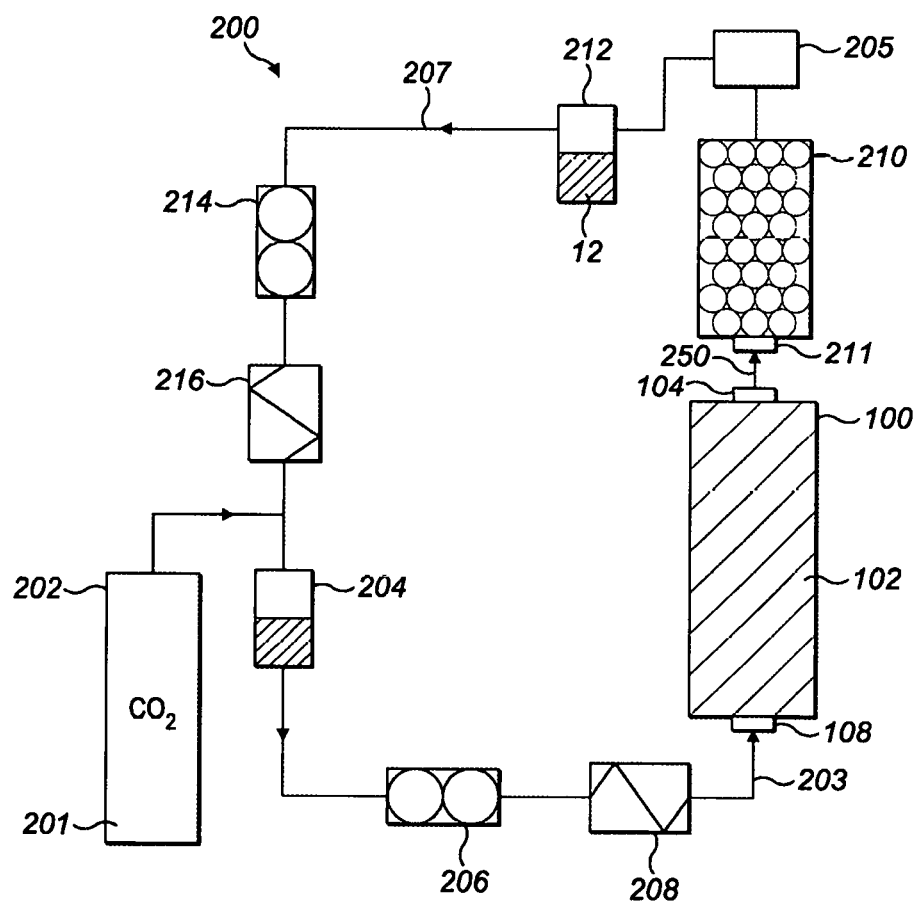
FIG. 5 is a schematic diagram illustrating apparatus for reclaiming anaesthetic agent captured in a canister according to an embodiment of the invention.

The canister 100 shown in FIG. 5 has been used to absorb an anaesthetic agent 12 which is bonded to the filter material 102 in the canister 100. A method for reclaiming the anaesthetic agent 12 from the filter material 102 is described herein with reference to FIG. 5 which shows a reclamation system 200 for retrieving agent 12 from the canister 100 according to an embodiment of the invention.

The reclamation system 200 exposes the filter material 102 to a supercritical fluid. In the current embodiment, supercritical $CO_2$ 203 is fed into the canister 100, wherein supercritical $CO_2$ 203 passes through the filter material 102. Liquid $CO_2$ 201 is fed into the system 200 from a liquid $CO_2$ tank 202 and collects in a $CO_2$ reservoir 204. A separation pump 206 pumps $CO_2$ 201 from the reservoir 204 into a separation condenser or accumulator 208 which pressurises and raises the temperature of the $CO_2$ 201 above its critical temperature and pressure to form supercritical $CO_2$ 203. The separation pump 206 and the accumulator 208 control the conditions under which the supercritical $CO_2$ 203 enters the canister 100.

The supercritical $CO_2$ 203 is fed into the egress conduit 108 of the canister 100 wherein it passes through the filter material 102. Volatile anaesthetic agent 12 bound to the filter material 102 will dissolve in the supercritical $CO_2$ 203, so that both the agent 12 and the supercritical $CO_2$ 203 form a supercritical solution 250. The supercritical $CO_2$ 203 acts to displace and dissolve the agent 12 from the filter material 102. The supercritical solution 250 exits the canister 100 through the ingress conduit 104.

The supercritical $CO_2$ 203 acts as a mobile phase, drawing supercritical agent 12 within it through a chromatography column 210. Chromatography columns may separate supercritical agent 12 based on polarity, molecular size and weight as discussed below. The supercritical solution 250 is supplied to an injector 211 which injects the supercritical solution 250 in aliquots into the chromatography column 210.

The pressure inside the canister 100 and the chromatography column 210 is maintained by a back-pressure regulator 205. After passing through the chromatography column 210, separated volatile anaesthetic agents 12 and $CO_2$ are released from their supercritical state and the volatile anaesthetic agents 12 are collected by cyclonic collection into a collection vessel 212. The gaseous $CO_2$ is subsequently re-compressed for re-use. The accumulator 208, canister 100 and chromatography column 210 are maintained at supercritical temperatures by one or more ovens (not shown). The cyclonic collector 212 may be maintained at cold temperatures to liquefy the anaesthetic agent 12 from the gaseous $CO_2$ 201.

The chromatography column 210 may be based on polarity, molecular size and weight and/or other molecular physiochemical differences that lead to different rates of flow under the influence of a supercritical fluid mobile phase. For example, a chromatography column with molecular size filters may lead to different retention times within the column that can separate different types of anaesthetic agents 12 from each other. Alternatively, a polarity based chromatography column may separate contaminants from supercritical solution 250. In an alternative embodiment of the invention, after injection of an aliquot of supercritical solution 250 for separation, pure supercritical $CO_2$ 203 may be provided to the column as the mobile phase (not shown).

In addition to capturing agent 12, the filter material 102 also captures contaminants, for example, water, urea, ammonia, formaldehyde, which may also be released into the supercritical solution 250. In the currently described embodiment, a polarity based chromatography column such as 2-PE (2-Ethyl Pyridine) is used to separate anaesthetic agents from contaminants.

The reclamation system 200 allows contaminants to be removed from the supercritical solution 250 via the chromatography column 210 and by cyclonic collection into the collection vessel 212.

It will be clear to those skilled in the art that more than one chromatography column 210 can be placed in series to perform different separations. If a plurality of anaesthetic agents 12 is absorbed by the filter material 102, a further chromatography column may be required after contaminants have been removed. In the preferred embodiment, a chromatography column 210 based on molecular size is used to separate anaesthetic agents. Monitoring of the product of one or more of the chromatography columns may be performed by infra-red monitoring equipment, such as those described herein. The flow of the product of one or more of the chromatography columns may be controlled by a controller, such as a computer to select volatile agents 12 and exclude contaminants where required.

When the canister 100 has been used to capture a single type of agent 12 and the risk of the filter material capturing contaminants is minimal, there is no need to use a chromatography column 210. Either the mixture of supercritical $CO_2$ and supercritical volatile anaesthetic agent 12 remains in a supercritical state for subsequent redelivery to the patient via the breathing circuit, or they are depressurised from supercritical conditions and the volatile anaesthetic agent 12 is collected by the cyclonic collector 212. The gaseous $CO_2$ is subsequently re-compressed for re-use, as described in detail below.

The gaseous $CO_2$ 207 flows into a recompression pump 214 which pumps the gaseous $CO_2$ 207 into a recompression condenser 216 which converts the gaseous $CO_2$ 207 into liquid $CO_2$ 201 which is stored in the $CO_2$ reservoir 204, or any excess is stored in the liquid $CO_2$ tank 202.

Figure 6:
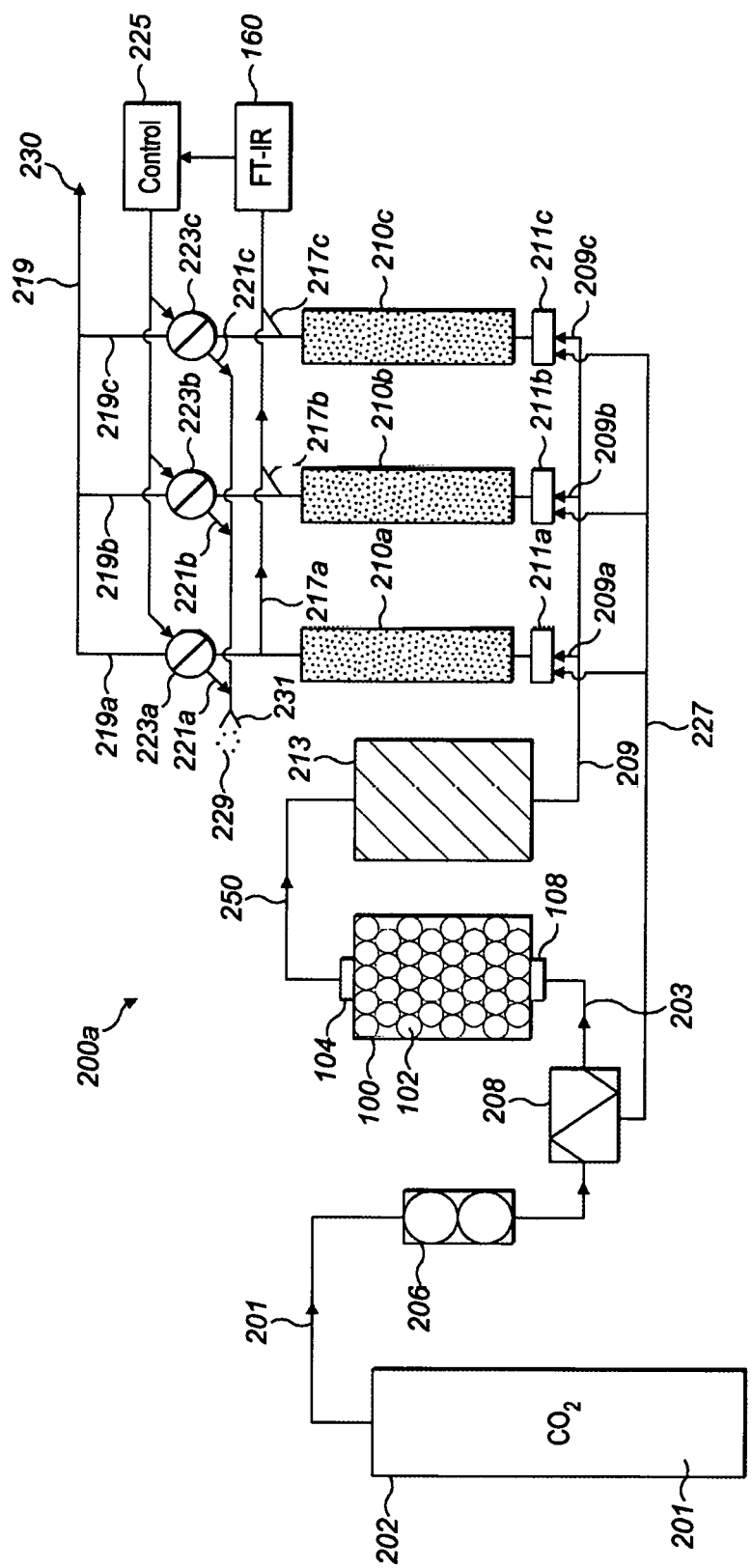
FIG. 6 is a schematic diagram illustrating alternative apparatus for reclaiming and purifying anaesthetic agent captured in a canister according to an embodiment of the invention.

FIG. 6 illustrates an alternative reclamation system 200*a* and method for extracting anaesthetic agent 12 from the filter material 102 of a canister 100 which comprises three chromatography columns: a first chromatography column 210*a*, a second chromatography column 210*b* and a third chromatography column 210*c*.

Liquid $CO_2$ 201 is fed into the system 200*a* from a liquid $CO_2$ tank 202. A pump 206 pumps $CO_2$ 201 from the liquid $CO_2$ tank 202 into a temperature-controlled accumulator 208. This pressurises and raises the temperature of the $CO_2$ 201 above its critical temperature and pressure to form supercritical $CO_2$ 203 and provides a reservoir to supply a constant flow of supercritical $CO_2$ 203. The pump 206 and the temperature-controlled accumulator 208 control the conditions under which the supercritical $CO_2$ 203 enters the canister 100.

The supercritical $CO_2$ 203 is fed into the egress conduit 108 of the canister 100 wherein it passes through the filter material 102 which has captured a plurality of volatile anaesthetic agents 12. Volatile anaesthetic agents 12 bound to the filter material 102 dissolve in the supercritical $CO_2$ 203, forming a supercritical solution 250. The supercritical solution 250 exits the canister 100 through the ingress conduit 104 and collects in a supercritical fluid collection vessel 213.

The supercritical solution 250 is fed into a main injection pipe 209, which feeds a first injection pipe 209*a*, a second injection pipe 209*b* and a third injection pipe 209*c*. The first injection pipe 209*a* supplies supercritical $CO_2$ 203 and agent 12 solution 250 to a first injector 211*a*; the second injection pipe 209*b* supplies supercritical $CO_2$ 203 and agent 12 solution 250 to a second injector 211*b*; and the third injection pipe 209*c* supplies supercritical $CO_2$ 203 and agent 12 solution 250 to a third injector 211*c*.

The first injector 211*a*, the second injector 211*b* and the third injector 211*c* are arranged to inject supercritical $CO_2$ 203 and agent 12 solution 250 aliquots into the first chromatography column 210*a*, the second chromatography column 210*b* and the third chromatography column 210*c* respectively.

Each Injection of solution 250 into each chromatography column is followed by a flow of pure supercritical $CO_2$ 203, which is supplied from the accumulator 208 via a supercritical $CO_2$ supply line 227. Supercritical $CO_2$ 203 acts as the mobile phase of the chromatography columns 210*a*, 210*b*, 210*c* which drives separation of anaesthetic agents 12 from contaminants. The chromatography columns aim to remove and separate hydrophilic contaminants such as methanol and formaldehyde and significantly different hydrophobic contaminants such as anaesthetic agent breakdown products from the supercritical solution 250; thereby maximising the purity of the agent 12 reclaimed by the invention.

In the presently described embodiment, the chromatography columns separate agents 12 based on polarity. Anaesthetic agents 12 have very similar polarities and are therefore eluted together. However, in alternative embodiments of the invention chromatography columns may be used which separate agents based on other characteristics such as size exclusion. For example, a molecular size exclusion chromatography column that distinguishes between the molecular sizes of the anaesthetic agents 12 may be used to separate agents from each other for subsequent collection in cyclonic collectors. Alternatively, chromatography columns may be placed in series to perform different separations on the same aliquot of supercritical solution 250.

The product produced by each chromatography column 210a, 210b, 210c is fed into a first chromatography egress pipe 217a, a second chromatography egress pipe 217b and a third chromatography egress pipe 217c respectively. Each chromatography egress pipe 217a, 217b, 217c is connected to a respective collection pipe 219a, 219b 219c and a respective waste pipe 221a, 221b, 221c. The first collection pipe 219a, the second collection pipe 219b and the third collection pipe 219c converge into a main collection pipe 219. The first waste pipe 221a, the second waste pipe 221b and the third waste pipe 221c converge into a main waste pipe 221 which leads to a waste vent 229. The flow of product through each chromatography egress pipe 217a, 217b, 217c is directed to either the respective collection pipe 219a, 219b 219c or the respective waste pipe 221a, 221b, 221c by a respective control valve 223a, 223b, 223c which are controlled by a valve controller 225.

An FT-IR device 160 monitors the product produced by each chromatography column 210a, 210b, 210c. When the FT-IR device 160 detects that agent 12 is being produced by the one or more chromatography columns 210a, 210b, 210c, the valve controller 225 sets the respective control valve(s) 223a, 223b, 223c so that the agent-product 230 flows through the respective collection pipe(s) 219a, 219b, 219c. In addition to anaesthetic agent 12, the product 230 produced by the one or more chromatography columns 210a, 210b, 210c also contains $CO_2$. The product 230 is in a supercritical state. The supercritical state is maintained by a back-pressure regulator 205, shown in FIGS. 7 and 8. All components including those downstream of the accumulator 208 are located in a temperature controlled environment (not shown) above the supercritical temperature of the fluid. In the preferred embodiment, the supercritical fluid is carbon dioxide and the temperature is 35° C., although other temperatures above the supercritical temperature of $CO_2$ could be used.

Alternatively, when the FT-IR device 160 detects that one or more chromatography columns 210a, 210b, 210c is no longer producing anaesthetic agent 12, the valve controller 225 sets the respective control valve(s) 223a, 223b, 223c so that the waste-product 231 flows through the respective waste pipe(s) 221a, 221b, 221c to the waste vent 229. The waste vent 229 allows the waste product 231 to change to the gas phase which is vented into the atmosphere.

The reclamation systems described herein typically operate at 7.4 MPa to 50 MPa (or higher). A preferred pressure is 10 MPa; and at 31° C. to 100° C. (or higher). A preferred temperature is 35° C. The reclamation systems described here may equally be used to reclaim agent 12 from a canister 101 described with reference to FIG. 3.

Figure 7:
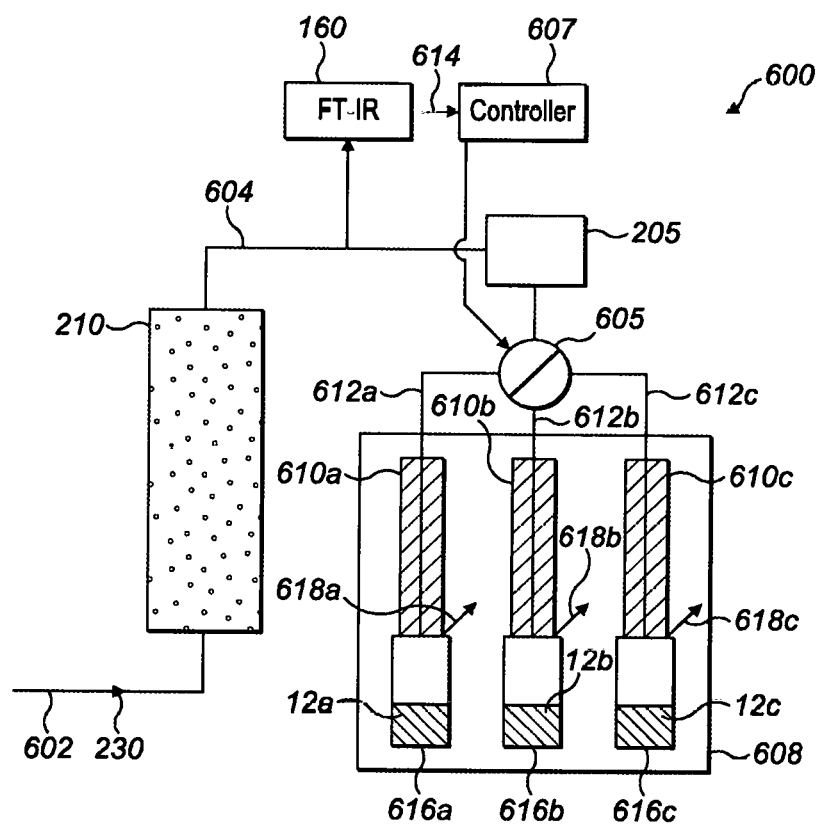
FIG. 7 is a schematic diagram illustrating apparatus for separating anaesthetic agents according to an embodiment of the invention.
Figure 8:
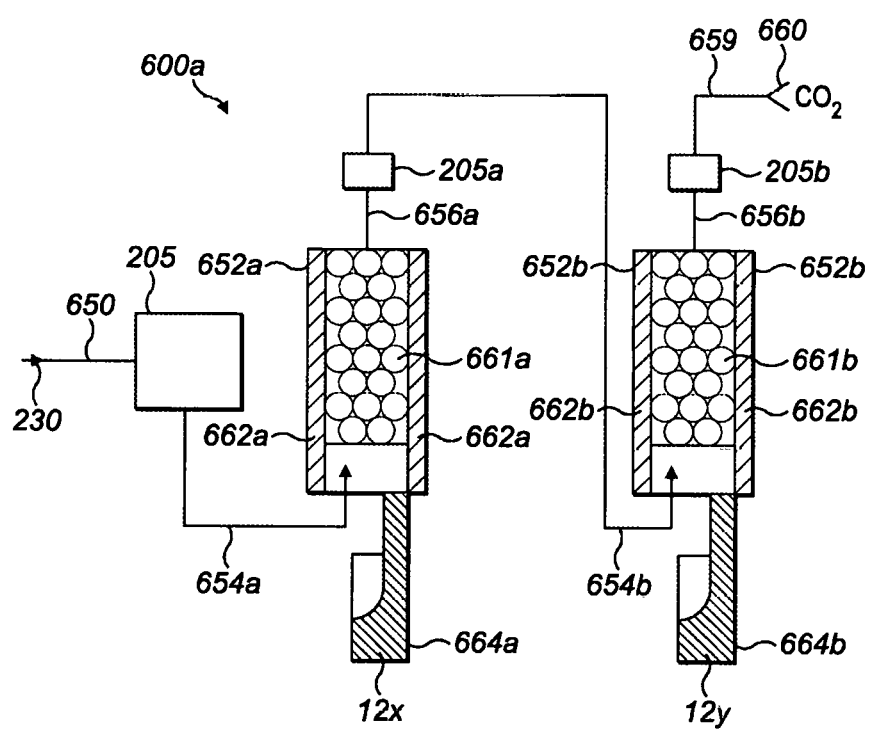
FIG. 8 is a schematic diagram illustrating alternative apparatus for separating anaesthetic agents according to an embodiment of the invention.

If a plurality of different anaesthetic agents 12 have been captured by the canister 100 shown in FIG. 6, the gas 230 produced by the one or more chromatography columns 210a, 210b, 210c will contain a plurality of anaesthetic agents 12. FIGS. 7 and 8 illustrate apparatus and methods for separating each agent 12 from a plurality of anaesthetic agents 12 contained in the gas 230.

FIG. 7 shows an agent collection system 600 in which one or more substances are separated from a supercritical solution comprising halocarbon and supercritical fluid. In the presently described embodiment, the supercritical solution is agent-product 230 from which one or more halocarbons are separated. Agent-product 230 is supplied to a chromatography column ingress pipe 602. The agent-product 230 contains three anaesthetic agents 12: agent A 12a; agent B 12b; and agent C 12c. The agents 12a, 12b 12c are dissolved in supercritical $CO_2$. Example agents include isoflurane, sevoflurane and desflurane.

The chromatography column ingress pipe 602 supplies agent-product 230 to a chromatography column 210. A chromatography column egress pipe 604 directs the product of the chromatography column 210 to a back-pressure regulator 205 to which a directional valve 605 is connected. The back-pressure regulator 205 depressurises the product of the chromatography column 210, which causes the product of the chromatography column 210 to cool. To mitigate the effects of cooling, the back-pressure regulator 205 contains a heating module (not shown) that prevents icing following decompression which may lead to sticking of the valve 605. The directional valve 605 is controlled by a controller 607. A FT-IR device 160 monitors the product produced by the chromatography column 210 by firing light through an in-line IR flow cell (not shown) located in the chromatography column egress pipe 604, and sends corresponding signals 614 to the controller 607, which is described further below.

The agent collection system 600 comprises a collection module 608, the interior of which is cooled by a temperature control system to liquefy the anaesthetic agent 12. The interior of the collection module 608 comprises three accumulators: a first heat accumulator 610a, a second heat accumulator 610b and a third heat accumulator 610c. Each heat accumulator 610a, 610b, 610c is connected to the directional valve 605 by a respective accumulator ingress pipe 612a, 612b, 612c.

The FT-IR device 160 ensures that each heat accumulator 610a, 610b, 610c collects a different agent. For example, when the FT-IR device 160 detects that agent A 12a is being produced by the chromatography column 210, the FT-IR device 160 sends a signal 614 to the controller 607 which in turn sets the valve 605 so that agent A 12a flows into the first accumulator 610a. If the FT-IR device 160 detects that that agent B 12b is being produced by the chromatography column 210, the FT-IR device 160 sends a signal 614 to the controller 607 which in turn sets the valve 605 so that agent B 12b flows into in the second accumulator 610b. Similarly, if the FT-IR device 160 detects that that agent C 12c is being produced by the chromatography column 210, the FT-IR device 160 sends a signal 614 to the controller 607 which in turn sets the valve 605 so that agent C 12c flows into the third accumulator 610c. Each heat accumulator 610a, 610b, 610c is arranged to transfer heat away from the anaesthetic agent gas 12a, 12b, 12c which are cooled and liquefy entering it which collects in an associated cyclonic collector 616a, 616b, 616c. Gaseous $CO_2$ is allowed to escape from each cyclonic collector 616a, 616b, 616c though an associated cyclonic vent 618a, 618b, 618c.

Alternative embodiments may contain further chromatography columns. Chromatography columns may separate based on polarity, molecular size or weight.

The preferred embodiment of the invention uses a size exclusion chromatography column with a pore size that differentiates between the different anaesthetic agents.

Alternatively, supercritical fractionation can be used to separate individual anaesthetic agents. This process refers to use of staged depressurisation of $CO_2$ and its use as a driving gas in cold fractionating columns to elute the different agents based on their volatility. Thus lower volatility fractions condense first during slow transit through the column. The more volatile fraction continues into the next column with $CO_2$. In this column, further cooling of the column causes condensation of this fraction and its separation from $CO_2$.

FIG. 8 shows an alternative agent collection system 600a which uses fractionation to separate anaesthetic agent 12 from agent-product 230. As above, the agent-product 230 is in a supercritical state when it enters the system 600a. The agent-product 230 flows along a pipe 650 to a back pressure regulator 205. Agent-product 230 is depressurised below critical pressure and warmed to prevent icing by the back-pressure regulator 205. Agent-product 230 flows to a first fractionating column 652a along a first fractionating column ingress pipe 654a.

A first fractionating column egress pipe 656a extends from the first fractionating column 652a to a first pressure reducing valve 205a. Pressure is further controlled by the downstream pressure-regulator valve 658a. A second fractionating column ingress pipe 654b extends from the first pressure reducing valve 658a to a second fractionating column 652b. A second fractionating column egress pipe 656b extends from the second fractionating column 652b to a second pressure reducing valve 205b. A vent pipe 659 extends from the second pressure reducing valve 205b to a vent 660.

Each fractionating column 652a, 652b comprises non-absorbent beads 661a, 661b, and a cooling jacket 662a, 662b to allow temperature control of each fractionating column 652a, 652b. A first collection vessel 664a is associated with the first fractionating column 652a, and a second collection vessel 664b is associated with the second fractionating column 652b.

The pressure of the solution 503 is lowered in stages by the pressure regulating valves 205a and 205b. Less volatile agent 12, for example Agent X 12x, is liquefied by the first fractionating column 652a and collects in the first collection vessel 664a. $CO_2$ and anaesthetic agent with a higher volatility, for example Agent Y 12y, passes into the second fractionating column 652b, which may be further depressurised by the pressure regulating valve 205b. Due to the low temperatures in the fractionating column 661b, the remaining anaesthetic agent liquefies and collects in the second collection vessel. Gaseous $CO_2$ is released via the vent 660. Alternatively, gaseous $CO_2$ may be recompressed for future use (not shown).

A plurality of fractionating columns may be arranged in parallel which enables selected agents to be recovered at a higher rate. Alternatively, a plurality of fractionating columns may be arranged in series, as shown in FIG. 8, to allow a greater range of agents to be collected.

Figure 9:
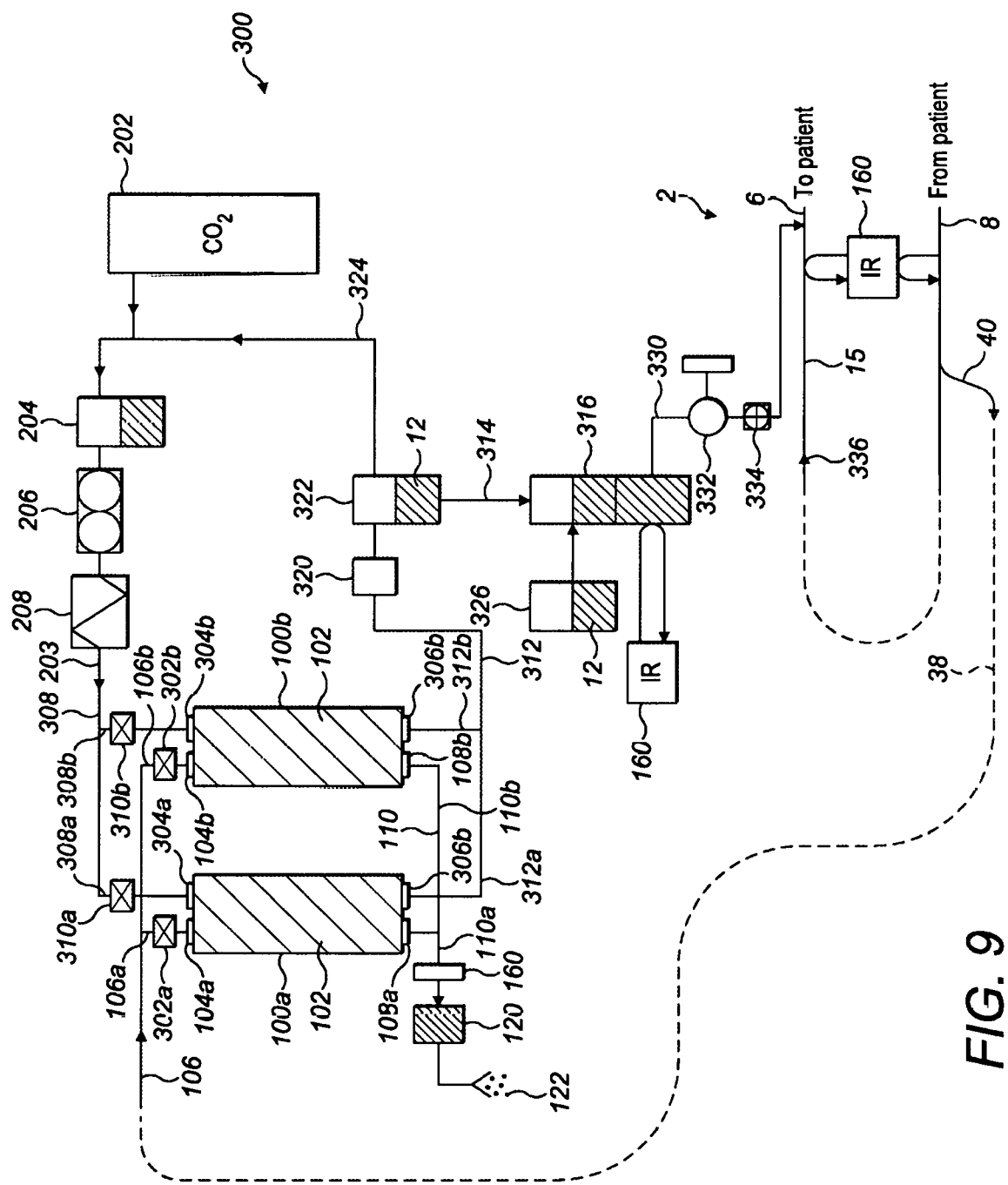
FIG. 9 is a schematic diagram illustrating apparatus for recycling anaesthetic agent for use in an anaesthetic machine according to an embodiment of the invention.

In alternative embodiments of the invention, in-line infrared, preferably FT-IR sensor, devices may be used to detect the presence of anaesthetic agents and contaminants in liquidised agent 12x, 12y. Further separation steps, for example using chromatography or fractional distillation, may then be used to achieve the required purity of agent 12x, 12y According to a further embodiment of the invention, a recycling system 300 for reintroducing halocarbon is shown in FIG. 9. The recycling system 300 comprises halocarbon-binding material, filter material 102 in the presently described embodiment, for capturing halocarbon from a gas. The system 300 is arranged to expose the material to gas containing halocarbon to capture the halocarbon, and to supercritical fluid to dissolve the halocarbon in a supercritical solution. In the presently described embodiment, the halocarbon is volatile anaesthetic agent 12 that has been extracted from the waste gas 38 of an anaesthetic machine, and returned back into the same anaesthetic machine, as shown in FIG. 9.

The recycling system 300 shown in FIG. 9 has a first module as described above, and the system 300 is arranged to supply fluid to the module so that the fluid passes through the filter material 102. The recycling system 300 offers the optimum in volatile anaesthetic agent 12 recycling to patients during long operations and in intensive care. The recycling system 300 is arranged to continually recycle a single volatile anaesthetic agent 12.

The recycling system 300 comprises a first silica aerogel canister 100a and a second silica aerogel canister 100b. Each canister 100a, 100b has a waste gas ingress conduit 104a, 104b to allow waste gas 38 to enter each canister 100a, 100b and a gas egress conduit 108a, 108b to allow processed gas to exit each canister 100a, 100b. The first waste gas ingress conduit 104a and the second waste gas ingress conduit 104b are each connected to a respective first waste gas ingress pipe 106a and second waste gas ingress pipe 106b. Each ingress pipe 106a, 106b comprises an ingress valve 302a, 302b for controlling the flow of waste gas 38 into the respective canister 100a, 100b. The first processed gas egress conduit 108a and the second processed gas egress conduit 108b are each removably connected to a respective first egress pipe 110a and second egress pipe 110b. The first and second egress pipes 110a, 110b meet to form a single main egress pipe 110 which comprises a Fourier transform infrared spectroscopy (FT-IR) device 160 arranged to detect the presence of volatile anaesthetic agent 12 in the main egress pipe 108. A rise in the concentration of volatile anaesthetic agent 12 in the main egress pipe 108 indicates that the canister currently removing agent 12 from the waste gas 38 is saturated which will necessitate a switch in the operation of the canisters 100a, 100b. After the gas has passed through the Fourier transform infrared spectroscopy (FT-IR) device 160, it then passes through a small activated charcoal filter 120 which captures any residual agent 12.

In addition to a waste gas ingress conduit 104a, 104b and processed gas egress conduit 108a, 108b each canister 100a, 100b has a supercritical $CO_2$ ingress port 304a, 304b and a supercritical $CO_2$ egress port 306a, 306b. Each $CO_2$ ingress port 304a, 304b is connected to a $CO_2$ ingress pipe 308a, 308b which supplies supercritical $CO_2$ 203 into each respective canister 100a, 100b. Each $CO_2$ ingress pipe 308a, 308b comprises a $CO_2$ valve 310a, 310b for controlling the flow of supercritical $CO_2$ 203 into each respective canister 100a, 100b. Each $CO_2$ ingress pipe 308a, 308b is fed from a main $CO_2$ ingress pipe 308. Each supercritical $CO_2$ egress port 306a, 306b is connected to a respective $CO_2$ egress pipe 312a, 312b. Each $CO_2$ egress pipe 312a, 312b is connected to a main $CO_2$ egress pipe 312 which carries supercritical $CO_2$ 203 from the first and second canisters 100a, 100b.

The main $CO_2$ egress pipe 312 leads to a back pressure regulator 320 that warms and decompresses the $CO_2$ and dissolved agent 12. A cooled cyclonic separation chamber 322 liquefies and separates the volatile agent 12 from the gaseous $CO_2$. The gaseous $CO_2$ flows in a recovered $CO_2$ pipe 324 to a $CO_2$ reservoir 204. A $CO_2$ tank 202 is connected to the recovered $CO_2$ pipe 324 to top-up the $CO_2$ in the recycling system 300. A separation pump 206 pumps $CO_2$ from the reservoir 204 into a separation accumulator 208. The separation pump 206 increases the pressure of the $CO_2$ above the critical pressure of $CO_2$ (73 bar). The accumulator 208 and canisters 100a, 100b are housed in an oven (not shown) to maintain the temperature above the critical temperature of $CO_2$ (31.1° C.). The accumulator 208 warms the $CO_2$ and provides a buffer of supercritical $CO_2$ to maintain the pressure in the circuit above critical pressure. Preferably the operating temperature is 35° C. and the pressure 100 bar (10 MPa). However, in alternative embodiments these values may be higher. The separation pump 206 and the accumulator 208 control the conditions under which the liquid $CO_2$ enters the main $CO_2$ ingress pipe 308.

The delivery chamber 316 is warmed above the critical temperature of $CO_2$ and stores agent 12 dissolved in supercritical $CO_2$ for use in a breathing circuit 2 of an anaesthetic machine. The delivery chamber 316 may receive injected recycled anaesthetic agent 12 from the cyclonic separator 322 via the delivery pipe 314 or from a container 326 containing non-recycled agent 12 which may have been obtained from another source. The anaesthetic agent 12 in the delivery chamber 316 is dissolved in supercritical $CO_2$. The concentration is measured by a Fourier transform infrared spectroscopy (FT-IR) device 160. Accordingly, the concentration of agent 12 in the supercritical $CO_2$ may be adjusted to the correct level by adding more or less agent 12 from the cyclonic separator 322 or container 326 or by adding supercritical $CO_2$ to the delivery chamber 316 from the separation pump 206 (connection not shown).

An injection pipe 330 extends from the delivery chamber 316 to the breathing circuit 2 of an anaesthetic machine. The injection pipe 330 comprises a warmed injector 334 under the influence of a computer and clinician-controlled valve 332. The injector injects agent 12 dissolved in supercritical $CO_2$ into the breathing circuit 2, preferably directly into the inspiration pipe 6. As the $CO_2$ is decompressed and warmed it vaporises and disperses the anaesthetic agent 12 for delivery to the patient. The soda lime canister 34 of the breathing circuit 2 may be moved to the inspiratory limb 6 to absorb the small amounts of $CO_2$ delivered by the injector 334.

A method of recycling halocarbon is now described with reference to FIG. 9. A patient breathes in gas containing volatile anaesthetic agent 12 supplied by the inspiration tube 6 of a breathing circuit 2 modified as described above and shown in FIG. 9. The patient exhales unused agent 12 via an expiratory tube 8. Waste gas 38 released by a pressure-relief valve 32 (not shown in FIG. 9) flows through the exhaust pipe 40 which is connected to a main ingress pipe 106 which splits into the first ingress pipe 106*a* and the second ingress pipe 106*b*. The first ingress valve 302*a* is open to allow waste gas 38 into the first canister 100*a* and the second ingress valve 302*b* is closed to prevent waste gas 38 from entering the second canister 100*b*. The waste gas 38 containing agent 12 is processed by the halocarbon-binding material to bind halocarbon to the material. The flow through the first canister 100*a* is as described above with reference to FIG. 2 and exits the first canister 100*a* via its egress port 108*a*. The processed gas 122 is released into the atmosphere via an activated charcoal filter 120.

The first $CO_2$ valve 310*a* is closed to prevent supercritical $CO_2$ entering the first canister 100*a* and the second $CO_2$ valve 310*b* is open to allow supercritical $CO_2$ to enter the second canister 100*b*. The material 102 is exposed to the supercritical $CO_2$ entering the second canister 100*b* which flows through the filter material 102 to dissolve halocarbon, i.e. the agent 12, bound to the material 102 by dissolving the agent 12 in the supercritical $CO_2$, as described above with reference to FIG. 5. The dissolved halocarbon and supercritical fluid to form a supercritical solution. The supercritical solution in which agent 12 is diluted exits the second canister 100*b* through the second supercritical $CO_2$ egress port 306*b*.

During processing of waste gas 38 by the current embodiment of the invention, the first ingress valve 302*a* and the first $CO_2$ valve 310*a* are arranged so that when the first ingress valve 302*a* is open the first $CO_2$ valve 310*a* is closed, and vice versa. Similarly, the second ingress valve 302*b* and the second $CO_2$ valve 310*b* are arranged so that when the second ingress valve 302*b* is open the second $CO_2$ valve 310*b* is closed, and vice versa. Accordingly, the valves 302*a*, 302*b*, 310*a*, 310*b* are arranged such that either of the first canister 100*a* or the second canister 100*b* cannot receive waste gas 38 and supercritical $CO_2$ simultaneously. In addition, during processing of waste gas 38 by the current embodiment of the invention, the first ingress valve 302*a* and the second ingress valve 302*b* are arranged so that they cannot be in the same state, i.e. open or closed at the same time. Similarly, the first $CO_2$ valve 310*a* and the second $CO_2$ valve 310*b* are arranged so that they cannot be in the same state, i.e. open or closed at the same time.

In an alternative embodiment, an ingress three-way valve located at the junction of the main ingress pipe 106, first ingress pipe 106*a* and second ingress pipe 106*b* may be substituted for each of the first and second ingress valves 302*a*, 302*b*. In addition, a three-way $CO_2$ valve located at the junction of the main supercritical $CO_2$ pipe 308, first supercritical $CO_2$ pipe 308*a* and second supercritical $CO_2$ pipe 308*b* may be substituted for the first and second supercritical $CO_2$ valves 310*a*, 310*b*.

The supply of waste gas 38 and supercritical $CO_2$ 302 entering the two canisters 100*a*, 100*b* of the recycling system 300 system is controlled by the valves 302*a*, 302*b*, 310*a*, 310*b* so that one canister 100*a*, 100*b* receives waste gas 38 while the other canister 100*b*, 100*a* receives supercritical $CO_2$ 203. Accordingly, one canister 100*a*, 100*b* captures agent 12 from the waste gas 38 while agent 12 is removed from the other canister 100*b*, 100*a* for re-use in the breathing circuit 2 of the anaesthetic machine.

The states in which the valves 302*a*, 302*b*, 310*a*, 310*b* operate are swapped simultaneously at regular intervals. In the embodiment of the invention shown in FIG. 9, during a first swap the first ingress valve 302*a* is closed, the first $CO_2$ valve 310*a* is opened, the second ingress valve 302*b* is opened and the second $CO_2$ valve 310*b* is closed. At a later point the states of the valves 302*a*, 302*b*, 310*a*, 310*b* are swapped back to their previous states when the filter material 102 of the first canister 102*a* is saturated. It is envisaged that in other embodiments of the invention the swap may occur before saturation of the filter material 102. When the states of the valves 302*a*, 302*b*, 310*a*, 310*b* are first swapped, the first canister 100*a* no longer receives waste gas 38, but receives supercritical $CO_2$ 203 instead to release the agent 12 captured in the canister 100*a*. The second canister 100*b* no longer receives supercritical $CO_2$ 203, but receives waste gas 38 instead to capture agent 12.

Swapping the states of the valves 302*a*, 302*b*, 310*a*, 310*b* and therefore the functions of the canisters 100*a*, 100*b* enables continuous operation of the agent recycling system 300. As mentioned above, the filter material 102 is able to withstand supercritical fluid. Therefore, the material and one or more modules according to an embodiment of the invention may be reused, i.e. be subject to many capture-reclamation cycles, without appreciable decay in their performance. However, in alternative embodiments of the invention, the filter material and/or one or more modules may require replacement after a number of capture-reclamation cycles. The agent 12 recovered by the recycling system 300 may be kept dissolved in supercritical $CO_2$ 203 which may be injected directly into the breathing circuit 2 of an anaesthetic machine as described above, or returned to a vaporiser (not shown).

Anaesthetic machines allow anesthetists to deliver a specific oxygen fraction with an accurately diluted amount of volatile agent 12 to the patient. The invention enables agent 12 to be rapidly administered to the patient with the required concentration. Providing volatile anaesthetic agent 12 directly into the breathing circuit 2 of the anaesthetic machine enables fast induction of the agent 12. The invention also provides an anaesthetist with fine control of the dosage of agent 12. An infra-red absorption spectra machine 160 monitors the concentrations of agent 12 in the inspiratory tube 6 and expiratory tube 8 of the breathing circuit 2. The concentration of agent 12 in the inspiratory tube 6 is monitored to ensure that the correct concentration of agent is administered to the patient. The concentration of agent 12 in the expiratory tube 8 is monitored as an Indicator of the depth of anaesthesia. For example, the level of end-tidal agent concentration is a reliable indicator of the depth of anaesthesia. The infra-red absorption spectra machine 160 is linked to a control module (not shown) that controls the delivery of the agent 12 by influencing the function of the delivery valve 332 based on the readings obtained by the infra-red absorption spectra machine 160.

The invention also enables the entire output from the patient to be scavenged for agent 12. Furthermore, the invention provides immediate clearance of agent 12 from the breathing circuit 2 and rapid wake-up of the patient.

Figure 10:
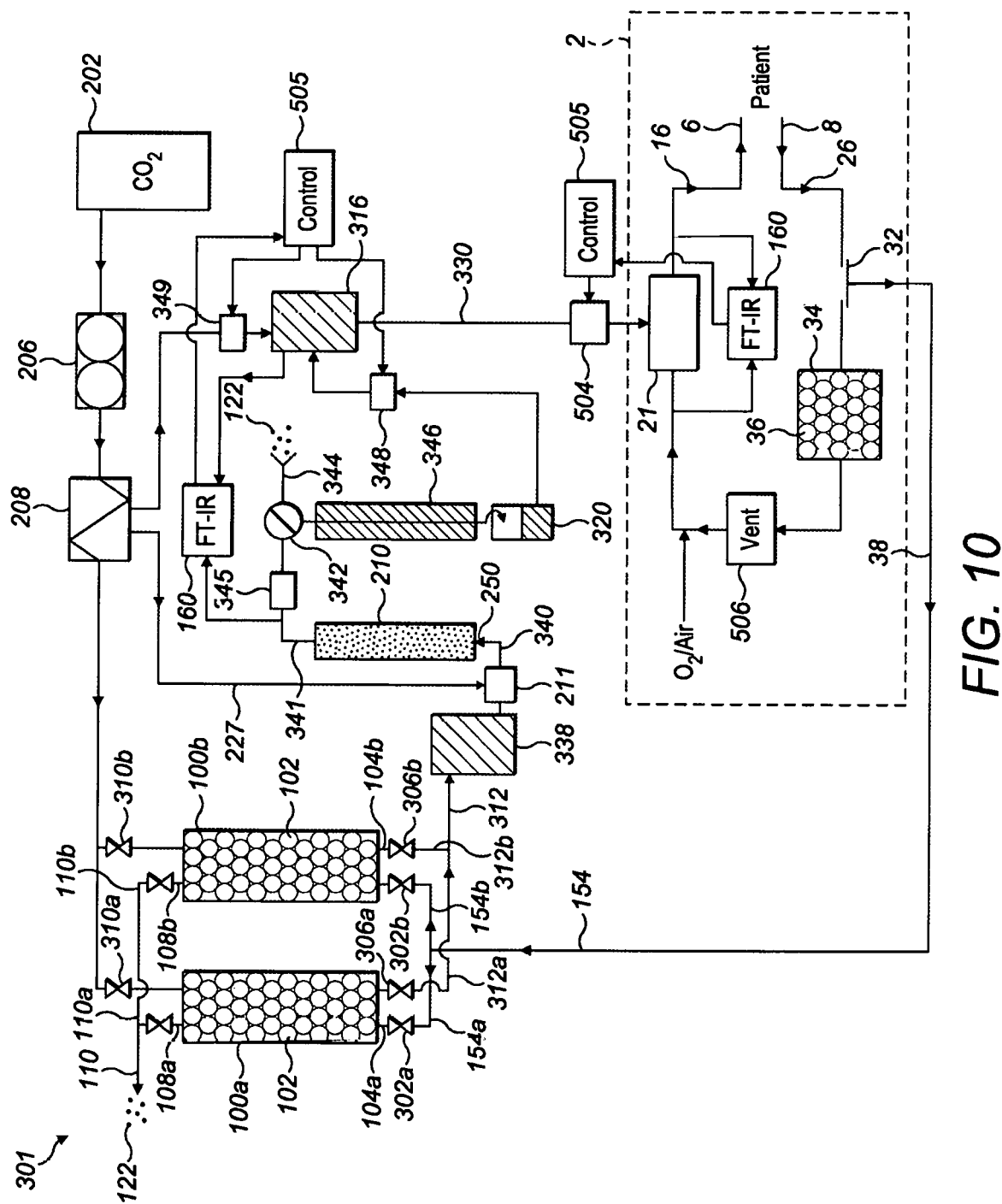
FIG. 10 is a schematic diagram illustrating alternative apparatus for recycling anaesthetic agent for use in an anaesthetic machine according to an embodiment of the invention.

FIG. 10 illustrates an alternative recycling system 301 which has many features in common with the apparatus described above. The alternative recycling system 301 delivers anaesthetic agent 12 dissolved in supercritical $CO_2$ 203 and recycles captured waste gas 38 itself, and comprises a chromatography column 210 to separate anaesthetic agent 12 from contaminates. The alternative recycling system 301 is preferably used with a single anaesthetic agent, although further chromatography or fractional distillation methods could be used to allow the use of multiple anaesthetic agents.

In the alternative recycling system 301 waste gas 38 from a breathing circuit 2 of an anaesthetic machine flows through a main ingress pipe 154 to the first and second canisters 100*a*, 100*b* via respective first and second ingress pipes 154*a*, 154*b*. In an alternative embodiment, the main ingress pipe 154 may also receive environmental air 107 from operating theatres.

According to a method of using the alternative recycling system 301, the first ingress valve 302*a* is open to allow waste gas 38 into the first canister 100*a* and the second ingress valve 302*b* is closed to prevent gas 38 entering the second canister 100*b*. The gas 38 is processed by the first canister 100*a* as described above to capture the agent 12 and exits the first canister 100*a* via its egress port 108*a*. The processed gas 122 is released into the atmosphere.

The first $CO_2$ valve 310*a* is closed to prevent supercritical $CO_2$ entering the first canister 100*a* and the second $CO_2$ valve 310*b* is open to allow supercritical $CO_2$ to enter the second canister 100*b*. Supercritical $CO_2$ entering the second canister 100*b* flows through the filter material 102 to reclaim agent 12 bound to the filter material 102 by dissolving the agent 12 in the supercritical $CO_2$ forming a supercritical solution 250. The supercritical solution 250 exits the second canister 100*b* through the second supercritical $CO_2$ egress port 306*b*, the second $CO_2$ egress pipe 312*b* and through the main $CO_2$ egress pipe 312 into a supercritical solution reservoir 338.

The supercritical solution reservoir 338 supplies supercritical solution 250 to a chromatography column injector 211 which injects aliquots of supercritical solution 250 into a chromatography column 210 via a chromatography column ingress pipe 340. A supply line 227 supplies pure supercritical $CO_2$ 203 to act as the mobile phase. A chromatography column egress pipe 341 allows fluids to leave the chromatography column 210. The chromatography column 210 separates contaminates from anaesthetic agent 12 and supercritical $CO_2$, and a mixture of anaesthetic agent 12 and supercritical $CO_2$ exits the chromatography column 210 via the chromatography column egress pipe 341.

The agent 12 dissolved in supercritical $CO_2$ flows along the chromatography column egress pipe 341 to a back-pressure regulator 345 which decompressed and warms the mixture. The decompressed mixture flows to a valve 342 which is controlled by a FT-IR device 160 which monitors the fluid in the chromatography column egress pipe 341. When the fluid in the chromatography column egress pipe 341 contains contaminates, the valve 342 releases any contaminants into the atmosphere via a chromatography column egress port 344. When the samples contain agent, the valve 342 directs the fluid flow to a heat accumulator 346 which transfers heat away from the fluid flow so that the anaesthetic agent 12 cools and liquefies for collection in a cyclonic separation chamber 320.

A controllable agent injector 348 controls the injection of liquefied agent into a delivery chamber 316. The FT-IR device 160 monitors the concentration of agent in the delivery chamber 316. The concentration of agent in the delivery chamber 316 may be adjusted by adding more agent 12 by the controllable agent injector 348 or more supercritical $CO_2$ 203 by a controllable supercritical $CO_2$ injector 349.

The supercritical $CO_2$ and agent at a controlled concentration are injected directly from the compression pipe 330 into the breathing circuit 2 by a warmed injector 504. An infra-red absorption spectra machine 160 monitors the concentrations of agent 12 in the inspiratory tube 6 and expiratory tube 8 of the breathing circuit 2. The infra-red absorption spectra machine 160 is linked to a controller 505 to ensure that the correct concentration of agent is administered to the patient. The controller 505 can also be influenced by the clinician. As the supercritical $CO_2$ is depressurised by the injector 504, it is warmed to prevent icing. This disperses and vaporises the anaesthetic agent 12 into the breathing circuit 2. Only small amounts of $CO_2$ are used and these are absorbed by the soda lime 36 in the breathing circuit 2.

Figure 11:
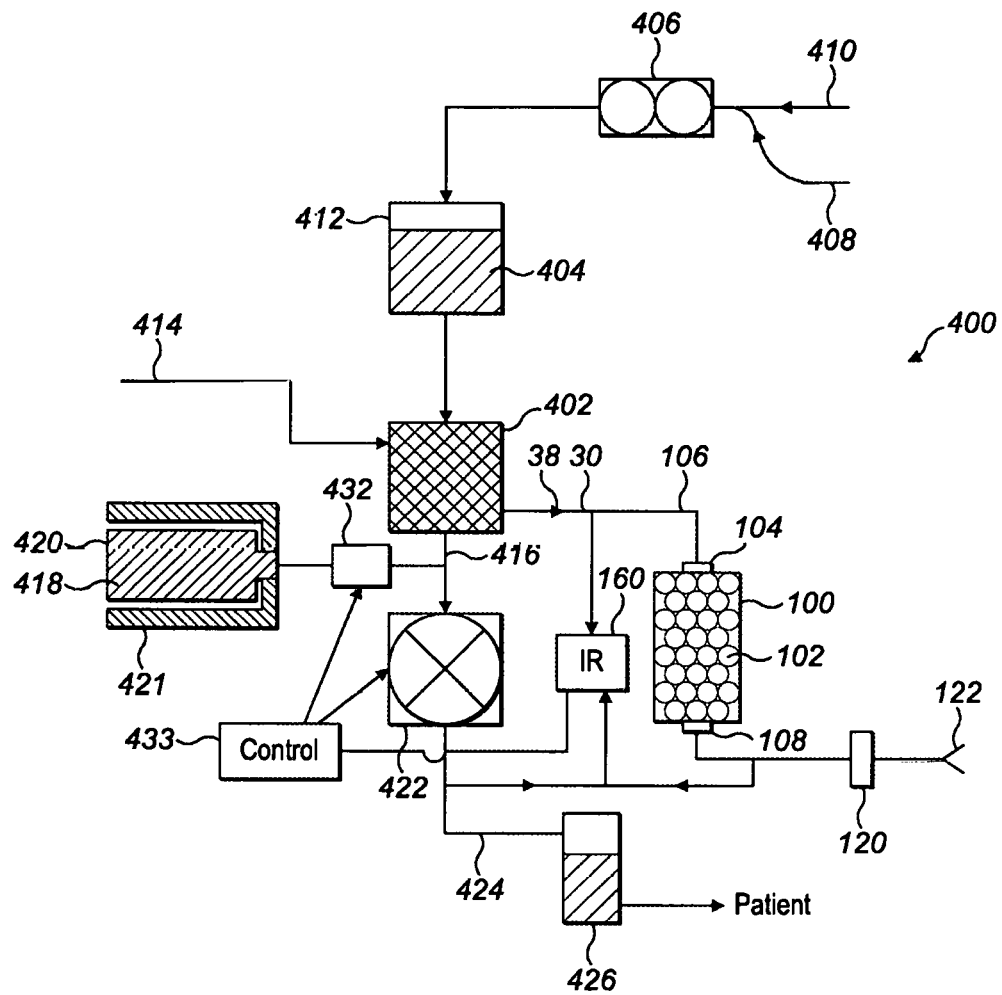
FIG. 11 is a schematic diagram illustrating apparatus for capturing anaesthetic agent for delivery to a cardiac bypass machine according to an embodiment of the invention.
Figure 12:
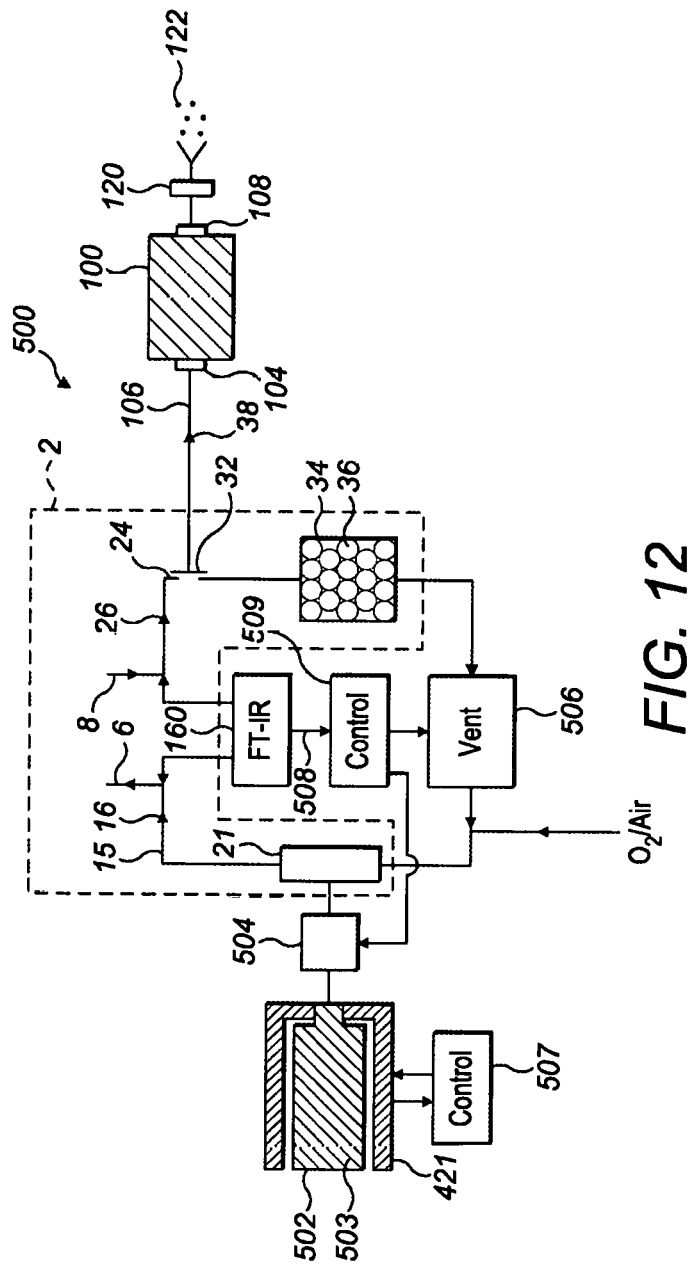
FIG. 12 is a schematic diagram illustrating the use of the invention for delivering anaesthetic agent to a breathing circuit in accordance with an embodiment of the invention.

According to another embodiment, the invention may be used to deliver a supercritical solution of anaesthetic agent dissolved in a supercritical fluid to a medical device. FIG. 11 illustrates a cardiac bypass circuit 400 comprising a pulmonary gas exchange 402, which is also known in the art as an oxygenator, which removes waste gas 38 from venous blood 404 while simultaneously oxygenating blood. A pump 406, a suction line 408 and a venous line 410 are used to take venous blood 404 from a patient during an operation. The venous blood 404 taken from the patient is collected in a blood reservoir 412 before entering the pulmonary gas exchange 402.

Oxygen and anaesthetic agent 12 are supplied to the pulmonary gas exchange 402 from an anaesthetic machine (not shown in FIG. 11) via an oxygen tube 414 and waste gas 38 exits the exchange 402 via an exhaust pipe 30. The waste gas 38 contains volatile anaesthetic agent 12 that has not been metabolised or absorbed by the patient. The exhaust pipe 30 is connected to an ingress pipe 106 which is removably connected to the ingress conduit 104 of a canister 100 as shown in FIG. 2 and described above. The canister 100 captures the agent 12 by binding the agent 12 to the filter material 102 as the waste gas 38 passed through the filter material, as described above with reference to FIG. 2. Waste gas 38 from which agent 12 has been removed by the canister 100 exits the canister 100 though the egress conduit 108 to which an egress pipe 110 is removably connected. The egress pipe 110 comprises a small activated charcoal filter 120 to capture any residual agent 12 in the processed gas 122 before the processed gas 122 is released from the egress pipe 110 into the atmosphere. Oxygenated blood from which the agent 12 has been removed exits the pulmonary gas exchange 402 via an exchange exit tube 416.

A supercritical solution 418 comprising supercritical $CO_2$ 203 and volatile anaesthetic agent 12 is stored in a pressurised storage tank 420 which is mounted in a heated sleeve 421 to maintain the temperature above critical temperature. The storage tank 420 supplies a warmed electronically controlled injector valve 432 which is controlled by a controller 433. The supercritical solution 418 is injected directly into the patient's blood flowing through the exchange exit tube 416. The supercritical $CO_2$ 203 is depressurised by the injector valve 432 and is absorbed into blood with the dispersed and vaporised anaesthetic agent 12. The blood-agent dilution flows from the exchange exit tube 416 into a centrifugal pump 422 which is controlled by the controller 433, and propels the blood containing the agent dilution into an arterial line 424 which feeds the blood-agent dilution into an artery of the patient. The arterial line 424 comprises a bubble trap 426 to prevent gas bubbles from entering the patient's circulatory system.

Samples of blood are taken from the arterial line 424 for analysis. The samples of blood are measured by an infra-red absorption spectra machine 160 to determine the concentration of agent 12 in the blood being returned to the patient. The concentration of agent 12 delivered into the exchange exit tube 416 may then be altered if necessary. The infra-red absorption spectra machine 160 also monitors the waste gas 38 from the pulmonary gas exchange 402 for volatile anaesthetic agent 12, which provides a means of measuring the depth of anaesthesia. In addition, the infra-red absorption spectra machine 160 monitors the processed gas 122 to indicate when the filter material 102 has been saturated with agent 12.

In alternative embodiments of the invention, either of the recycling systems 300, 301 described above may be combined with the cardiac bypass circuit 400 to form a recycling system for reintroducing volatile anaesthetic agent that has been extracted from the blood of a patient by the cardiac bypass circuit 400. In further embodiments of the invention, a mixture of anaesthetic and supercritical $CO_2$ may be injected into the gas feed to the oxygenator or the arterial line 424 of a cardiac bypass circuit 400. This invention may also be used in mini-bypass circuits that do not have a venous blood reservoir 412.

In a further embodiment, the invention may be used in a portable anaesthetic machine 500, such as may be used by the military, disaster relief organisations or hospitals, as shown in FIG. 12. The portable anaesthetic machine 500 comprises a replaceable pressurised storage tank 502 containing a supercritical solution 503 of anaesthetic agent dissolved in supercritical $CO_2$. The replaceable storage tank 502 is mounted in a warming sleeve 421 which ensures that the solution is maintained at a supercritical temperature. The warming sleeve is controlled by a warming sleeve controller 507.

The storage tank 502 feeds an injector 504 controlled by an injector system controller 509 which injects solution 503 into a vaporisation chamber 21 which is incorporated into the breathing circuit 2 of the portable anaesthetic machine 500. The unidirectional valve 16 is connected to an inspiratory tube 6 which is arranged to supply gas containing an anaesthetic agent 12 for inhalation by a patient. The portable anaesthetic machine 500 comprises an expiratory tube 8 through which exhaled and unused gases and agent 12 are transported away from the patient via a unidirectional expiratory valve 26 to an expiratory pipe 24.

A $CO_2$ absorber canister 34 is connected to the expiratory pipe 24. The absorber canister 34 contains lime soda 36 to absorb carbon dioxide from the gas that flows through the canister 34. A ventilator or bag 506 links the $CO_2$ absorber canister 34 to the vaporisation chamber to complete the breathing circuit 2 and provide a means of pressuring the breathing circuit 2 to deliver a breath to the patient.

The portable anaesthetic machine 500 comprises an infra-red monitoring device. In the presently described embodiment a FT-IR device 160 is used which is arranged to monitor the level of agent 12 flowing in the inspiratory pipe 6 and the expiratory pipe 8. In alternative embodiments of the invention, the infra-red monitoring device may be a dispersive infra-red device to improve portability as dispersive infra-red devices are typically simpler and smaller than a FT-IR device. If the FT-IR device 160 detects that the level of agent in the flowing in each of the inspiratory pipe 6 and the expiratory pipe 8 requires adjustment, it sends a signal 508 to the controller 509 which instructs the injector 504 to increase or reduce the injection of solution 503, as necessary. The controller 509 also adjusts the ventilator to deliver the required pressure and rate for ventilation as decided by the clinician.

A pressure release valve 32 directs waste gas 38 through an ingress pipe 106 to an ingress conduit 104. The waste gas 30 is processed by a canister 100 containing filter material 102 which captures agent 12. Processed gas 122 exits the canister 100 via an egress conduit 108, flows through an activated charcoal filter 120 and vented into the atmosphere.

In alternative embodiments of the invention, a catalyst may be deposited onto a ceramic honeycomb structure at the ingress conduit 104 of the canister 100. In this position, the catalyst will act on d supercritical solution as it egresses the canister 100 during reclamation. In further embodiments, the catalyst is introduced as a dopant into an aerogel. It will be clear to those experienced in the art, that many different precious and non-precious metals might be used as a catalyst.

Although particular embodiments of the invention have been disclosed herein in detail with reference to a medical environment, this by way of example only and for the purposes of illustration only. The invention may be used for the capture and reclamation of halocarbons in other industries in which halocarbon capture and/or reuse is desirable or required.

In an alternative embodiment of the invention, exhaust gas from the production area of a factory which uses halocarbons is passed through a canister 100, 101 containing filter material. The halocarbons are captured by the filter material. Once the filter material has been saturated, it may be subjected to supercritical $CO_2$, as described above, to dissolve the halocarbons in the supercritical $CO_2$ to produce a supercritical solution. The halocarbons may be separated from the supercritical $CO_2$ by chromatography and fractional distillation, as described above.

Nitrous oxide ($N_2O$) is an important gas in pediatric and maternal anaesthesia. However, $N_2O$ is unstable under supercritical conditions, but may be controlled when used with a reduction catalyst.

In a further embodiment of the invention, the module 90 may comprise a reduction catalyst such as precious or semi-precious metals/metal oxides. In a preferred embodiment, the metal catalyst is platinum although others such as titanium oxide, tungsten oxide, vanadium oxide, molybdenum oxide, rhodium, palladium may be used. The reduction catalyst may be deposited onto the filter material 102, which may preferably be aerogel or any of the other filter materials described above. Alternatively, the filter material 102 may comprise the reduction catalyst. The reduction catalyst may be loaded with reactant, preferably urea before halocarbon capture or before halocarbon reclamation by supercritical $CO_2$ extraction. In this way, as waste gas 38 containing agent 12 passes into the module, nitrous oxide may react with the urea ($CO(NH_2)_2$) in the presence of the catalyst to form nitrogen ($N_2$), water ($H_2O$) and carbon dioxide ($CO_2$).

When the canister 100 is saturated with agent 12, it may be flushed with supercritical $CO_2$ to elute the halocarbon agent 12 as described in FIGS. 5, 6, 9 and 10. In the present embodiment, due to the presence of nitrous oxide absorbed onto the filter material and the selective reduction catalysts, it will also reduce nitrous oxide. Carbon dioxide is pumped into the canister to achieve supercritical pressure, preferably at 10 MPa and 35° C. degrees, although higher pressures and temperatures may be required. When the circuit is pressurised, flow through the system when the back pressure regulator opens results in supercritical $N_2O$ diluted in supercritical $CO_2$ passing through the filter material and catalyst in the presence of urea. Reaction rates are high at supercritical pressure and temperature and in the absence of oxygen. Nitrogen gas and other by-products may be extracted from the agent by chromatographic separation.

It will clear to those skilled in the art that this invention may be used for the selective reduction catalysis of nitrous oxide intermediates ($NO_x$) including nitrous oxide ($N_2O$) in situations outside of the reclamation of anaesthetic agents, such as power or heat generation and in the automobile industry.

In other embodiments of the invention other supercritical fluids such as supercritical nitrous oxide ($N_2O$) may be used. $N_2O$ becomes supercritical at a similar temperature and pressure as $CO_2$ and behaves in a similar manner to supercritical $CO_2$. For example, in an alternative embodiment of the invention described above, supercritical $N_2O$ may be used to dissolve agent 12 bound to the filter material 102 in an alternative canister 100, 101 that has been saturated with agent 12. In these embodiments, it is envisaged that reduction catalysts as described above will be used to reduce $N_2O$ to nitrous and oxygen, and/or supercritical $N_2O$ may be diluted in supercritical $CO_2$ to stabilise supercritical $N_2O$.

The aforementioned embodiments are not intended to be limiting with respect to the scope of the appended claims, which follow. Furthermore, features of one or more of the above embodiments may be readily combined with one or more features of another embodiment. It is also contemplated by the inventors that various substitutions, alterations, and modifications may be made to the invention without departing from the scope of the invention as defined by the claims.

The invention claimed is:

1. A method for recovering volatile anaesthetic agent from a filter, comprising subjecting the filter to a supercritical fluid, wherein the agent is dissolved in the supercritical fluid thereby forming a supercritical solution which carries the agent from the filter, wherein subsequently the volatile anaesthetic agent is separated from the supercritical solution.

2. The method as claimed in claim 1, in which the method further comprises removing contaminants from the supercritical solution.

3. A method as claimed in claim 1, in which the supercritical fluid is carbon dioxide or nitrous oxide.

4. The method as claimed in claim 1, in which the anaesthetic agent comprises a plurality of different volatile anaesthetic agents.

5. The method as claimed in claim 4, in which the method comprises separating the plurality of different volatile anaesthetic agents from each other.

6. The method as claimed in claim 1, further comprising one or more separations performed by chromatography, said one or more separations being one or more of: removing contaminants from the supercritical solution; and separating different volatile anaesthetic agents from each other.

7. The method as claimed in claim 6, in which the separation uses supercritical fluid as a separating agent or mobile phase.

8. The method as claimed in claim 1, further comprising one or more separations performed by fractionation, said separations being one or more of: removing contaminants from the supercritical solution; and separating different volatile anaesthetic agents from each other.

9. The method as claimed in claim 8, in which fractionation is driven by the supercritical fluid.

10. The method as claimed in claim 1, comprising one or more separations and monitoring product produced by a separation.

11. The method as claimed in claim 10, in which product is monitored by one or more of infrared spectroscopy, mass spectroscopy, UV detection, Raman spectroscopy, acoustic resonance spectroscopy, or piezoelectric crystal resonance.

12. The method as claimed in claim 1, in which the method comprises collecting one or more types of anaesthetic agent from the supercritical fluid.

13. The method as claimed claim 12, in which a cooled cyclonic collector is used to collect the, or each, agent.

14. The method as claimed in claim 1, in which the supercritical fluid is carbon dioxide and in which agent is separated from the supercritical carbon dioxide by depressurisation of the supercritical solution below the critical pressure of carbon dioxide at temperatures below the critical temperature of carbon dioxide to form carbon dioxide gas and to selectively condense one or more agent fractions from the gaseous carbon dioxide.

15. The method as claimed in claim 1, in which gas including the anaesthetic agent is passed through the filter so that agent binds thereto.

16. The method as darned in claim 15, in which the gas is from a medical environment and/or from an anaesthetic machine.

17. The method as claimed in claim 1, in which the filter comprises one or more of aerogel, silicon dioxide, zeolite, carbon, and activated carbon.

18. The method as claimed in claim 1, in which the supercritical fluid is at a pressure between 7 MPa and 50 MPa.

19. The method as claimed in claim 1, in which the supercritical fluid is at a temperature between 30° C. and 100° C.

20. The method as claimed in claim 1, in which the agent is separated from the supercritical solution by depressurisation of the supercritical solution below the critical pressure of the supercritical fluid at temperatures below the critical temperature of the supercritical fluid to form a gas phase of the supercritical fluid and to selectively condense one or more agent fractions from the gas phase of the supercritical fluid.

21. An apparatus for recovering anaesthetic agent from a gas, comprising a module housing filter material and into which gas can pass so that agent binds to the filter, the module being resistant to supercritical fluid and able to withstand supercritical pressure and temperature so as to enable captured agent to be reclaimed by exposure to supercritical fluid.

22. The apparatus of claim 21, in which the module is able to withstand a pressure between 7 MPa and 50 MPa.

23. The apparatus of claim 21, in which the module is able to withstand a temperature between 30° C. and 100° C.

24. The apparatus of claim 21, in which the module is able to withstand a pressure between 7 MPa and 50 MPa and a temperature between 30° C. and 100° C.

25. A method for recycling volatile anaesthetic agent from a gas derived from a patient in a medical environment, comprising the steps of:
    passing the gas through a filter so that anaesthetic agent becomes bound thereto;
    subjecting the filter material to a supercritical fluid, thereby forming a supercritical solution;
    removing contaminants from the supercritical solution;
    collecting the anaesthetic agent from the supercritical solution; and
    reintroducing the anaesthetic agent to a patient.

26. The method as claimed in claim 25, in which the supercritical fluid is at a pressure between 7 MPa and 50 MPa when the filter material is subjected to the supercritical fluid.

27. The method as claimed in claim 25, in which the supercritical fluid is at a temperature between 30° C. and 100° C. when the filter material is subjected to the supercritical fluid.

28. The method as claimed in claim 25, in which the anaesthetic agent is collected from the supercritical solution by depressurisation of the supercritical solution below the critical pressure of the supercritical fluid at temperatures below the critical temperature of the supercritical fluid to form a gas phase of the supercritical fluid and to selectively condense one or more agent fractions from the gas phase of the supercritical fluid.

* * * * *